US012697343B2

(12) United States Patent
Bianchi et al.

(10) Patent No.: US 12,697,343 B2
(45) Date of Patent: Aug. 4, 2026

(54) INTRAVENOUS ISTAROXIME FOR THE TREATMENT OF ACUTE HEART FAILURE

(71) Applicant: Seismic Pharmaceuticals Operations LLC, Warrington, PA (US)

(72) Inventors: Giuseppe Bianchi, Milan (IT); Patrizia Ferrari, Varese (IT); Mara Ferrandi, Milan (IT); Paolo Barassi, Castelveccana (IT)

(73) Assignee: Seismic Pharmaceuticals Operations LLC, Warrington, PA (US)

( * ) Notice: Subject to any disclaimer, the term of this patent is extended or adjusted under 35 U.S.C. 154(b) by 427 days.

(21) Appl. No.: 18/273,143

(22) PCT Filed: Jan. 21, 2022

(86) PCT No.: PCT/US2022/013278

§ 371 (c)(1),
(2) Date: Jul. 19, 2023

(87) PCT Pub. No.: WO2022/159678

PCT Pub. Date: Jul. 28, 2022

(65) Prior Publication Data

US 2024/0293426 A1 Sep. 5, 2024

Related U.S. Application Data

(60) Provisional application No. 63/140,552, filed on Jan. 22, 2021.

(51) Int. Cl.

| | |
|---|---|
| ***A61K 31/5685*** | (2006.01) |
| ***A61K 9/00*** | (2006.01) |
| ***A61P 9/04*** | (2006.01) |

(52) U.S. Cl.

CPC ........ *A61K 31/5685* (2013.01); *A61K 9/0019* (2013.01); *A61P 9/04* (2018.01)

(58) Field of Classification Search

CPC .................................................. A61K 31/5685

See application file for complete search history.

(56) References Cited

U.S. PATENT DOCUMENTS

| | | | |
|---|---|---|---|
| 4,534,899 A | 8/1985 | Sears | |
| 5,846,743 A | 12/1998 | Janmey et al. | |
| 5,874,268 A | 2/1999 | Meyer | |
| 6,007,839 A | 12/1999 | Mayhew et al. | |
| 6,063,400 A | 5/2000 | Geho et al. | |
| 6,261,815 B1 | 7/2001 | Meyer | |
| 6,384,250 B2 | 5/2002 | Gobbini | |
| 6,589,503 B1 | 7/2003 | Piwnica-Worms | |
| 7,109,034 B2 | 9/2006 | Orwar et al. | |
| 7,306,783 B2 | 12/2007 | Piwnica-Worms | |
| 11,197,869 B2 * | 12/2021 | Bianchi | A61P 9/04 |
| 11,583,540 B2 * | 2/2023 | Bianchi | A61K 31/5685 |
| 2004/0028670 A1 | 2/2004 | Carlson et al. | |
| 2004/0151766 A1 | 8/2004 | Monshan et al. | |
| 2005/0136121 A1 | 6/2005 | Kershman et al. | |
| 2006/0083737 A1 | 4/2006 | Minomi et al. | |
| 2007/0042031 A1 | 2/2007 | Maclachlan et al. | |
| 2007/0077286 A1 | 4/2007 | Ishihara et al. | |
| 2007/0082042 A1 | 4/2007 | Park et al. | |
| 2007/0110788 A1 | 5/2007 | Drummond et al. | |
| 2011/0097401 A1 | 4/2011 | Phillips et al. | |
| 2017/0298107 A1 | 10/2017 | Olson et al. | |

FOREIGN PATENT DOCUMENTS

| | | |
|---|---|---|
| CN | 103315968 B | 4/2016 |
| EP | 0826197 B1 | 2/1998 |
| WO | WO2010/149666 A1 | 12/2010 |
| WO | WO2020/180356 A9 | 9/2020 |

OTHER PUBLICATIONS

Carubelli et al. European Journal of Heart Failure, 2020, 22(9): 1684-1693.*

Abraham et al., "In-hospital mortality in patients with acute decompensated heart failure requiring intravenous vasoactive medications: an analysis from the Acute Decompensated Heart Failure National Registry (Adhere)" J Am Coll Cardiol 46:57-64 (2005).

Alemanni et al. "Role and mechanism of subcellular Ca2+ distribution in the action of two inotropic agents with different toxicity" J Mol Cell Cardiol 50:910-8 (2011).

Al-Muhammed, "In-vivo studies on dexamethasone sodium phosphate liposomes" J. Microencapsul. 13:293-306 (1996).

Asahi et al., "Transmembrane helix M6 in sarco(endo)plasmic reticulum Ca(2+)-ATPase forms a functional interaction site with phospholamban. Evidence for physical interactions at other sites" J Biol Chem 274: 32855-32862 (1999).

Ashkar & Makaryus, "Dobutamine", In StatPearls [Internet], Treasure Island (FL): StatPearls Publishing, Jan. 2017-2018 (available at https://www.ncbi.nlm.nih.gov/books/NBK470431/).

Baheti et al., "Excipients used in lyophilization of small molecules" J. Excipients and Food Chem. 1(1):41-54 (2010).

Bers et al., "Regulation of Ca2+ and Na+ in normal and failing cardiac myocytes" Ann N.Y. Acad Sci 2006; 1080:165-177 (2006).

Bers, "Altered cardiac myocyte Ca regulation in heart failure" Physiology 21: 380-387 (2006).

Bers, "Calcium cycling and signaling in cardiac myocytes" Annu Rev Physiol 70:23-49 (2008).

Braunwald, "The war against heart failure: the Lancet lecture" 2015; 385:812-24 (2015).

Brophy et al., "Bioavailability of oral dexamethasone during high dose steroid therapy in neurological patients" Eur. J. Clin. Pharmacol. 24:103-108 (1983).

(Continued)

*Primary Examiner* — Rei Tsang Shiao

(74) *Attorney, Agent, or Firm* — Myers Bigel, P.A.

(57) ABSTRACT

Described herein are methods of treating acute heart failure in a subject in need thereof, comprising administering a therapeutically effective amount of istaroxime by intravenous infusion over a period of at least 24 hours wherein the therapeutically effective amount of istaroxime is between about 0.1 µg/kg/min and about 3.0 g/kg/min; and wherein the subject's acute heart failure is treated.

19 Claims, 11 Drawing Sheets

(56) References Cited

OTHER PUBLICATIONS

Bonsu el al., "Pharmacological treatments for heart failure with preserved ejection fraction—a systematic review and indirect comparison" Heart Failure Reviews 23:147-156 (2018).
Butler et al., "Past, present, and future of acute heart failure clinical trials—a high-risk population in search of a strategy" Eur J Heart Fail.20(5):839-841 (2018).
Byrne et al., "Recirculating cardiac delivery of AAV2/1SERCA2a improves myocardial function in an experimental model of heart failure in large animals" Gene Therapy 15:1550-1557 (2008).
Campia et al. "Acute Heart Failure with Low Cardia Output: Can We Develop a Short-term Inotropic Agent that Does Not Increase Adverse Events?" Curr, Heart Fall. Rep. 7:100-109 (2010).
Carillion et al., "Atorvastatin reduces β-Adrenergic dysfunction in rats with diabetic cardiomyopathy" PloS One e0180103 (2017).
Choi et al., "Defective intracellular Ca2+ signaling contributes to cardiomyopathy in Type 1 diabetic rats" Am. J. Physiol. Heart Cir. Physiol 283:H1398-H1408 Sep. 2002).
Chonn & Cullis, "Recent advances in liposomal drug-delivery systems" Curr. Opin. Biotechnol. 6:698-708 (1995).
De Munari et al., "Structure-based design and synthesis of novel potent Na+, K+-ATPase inhibitors derived from a 5alpha,14alpha-androstane scaffold as positive inotropic compounds" J. Med. Chem. 46(17): 3644-3654 (2003).
Do Carmo et al., "Chronic central leptin infusion restores cardiac sympathetic-vagal balance and baroreflex sensitivity in diabetic rats" Am. J. Physiol. Heart Cir. Physiol 295:H1974-1981 (2008).
Evangelista et al., "European Association of Echocardiography recommendations for standardization of performance, digital storage and reporting of echocardiographic studies" Eur J Echocardiogr 9(4):438-48 (2008).
Fernandez-Tenorío & Niggli, "Stabilization of Ca 2+ signaling in cardiac muscle by stimulation of SERCA" J Mol Cell Cardiol. 119:87-95 (2018).
Ferrandi et al., "Renal Na,K-ATPase in genetic hypertension" Hypertension 28(6):1018-25 (1996).
Ferrandi et al., "Istaroxime stimulates SERCA2a and accelerates calcium cycling in heart failure by relieving phospholamban inhibition" Br J Pharmacol 169:1849-61 (2013).
Flaherty et al., "Acute heart failure syndromes in patients with coronary artery disease early assessment and treatment" J Am Coll Cardiol. 53(3):254-63 (2009).
Fotherby, "Bioavailability of orally administered sex steroids used in oral contraception and hormone replacement therapy" Contraception 54:59-69 (1996).
Georghiade et al., "Hemodynamic, Echocardiographic, and Neurohormonal Effects of Istaroxime, a Novel Intravenous Inotropic and Lusitropic Agent" J Am Coll Cardiol.51:2276-85 (2008).
Ghio et al., "Independent and additive prognostic value of right ventricular systolic function and pulmonary artery pressure in patients with chronic heart failure" J Am Coll Cardiol 37(1):183-8 (2001).
Gong et al., "Levosimendan Treatment for Heart Failure: A Systematic Review and Meta-Analysis" J Cardiothorac Vasc Anesth 29:1415-25 (2015).
Größl et al., "A novel artificial microRNA expressing AAV vector for phospholamban silencing in cardiomyocytes improves Ca2+ uptake into the sarcoplasmic reticulum" PLoS One 9:e92188 (2014).
Guido et al., "The Effects of Diabetes Induction on the Rat Heart: Differences in Oxidative Stress, Inflammatory Cells, and Fibrosis between Subendocardial and Interstitial Myocardial Areas" Oxid Med Cell Longev.2017: 5343972 (Epub Jul. 11. 2017).
Gulati et al., "Mitral annular descent velocity by tissue Doppler echocardiography as an index of global left ventricular function" Am J Cardiol. 77(11):979-84 (1996).
Haddad et al., "Right ventricular function in cardiovascular disease, part II: pathophysiology, clinical importance, and management of right ventricular failure" Circulation 117(13):1717-31 (2008).
Heineke & Molkentin, "Regulation of cardiac hypertrophy by intracellular signalling pathways" Nat Rev 7:589-600 (2006).
Hidalgo-Aragones et al., "Pharmacokinetics of oestrone-3-O-sulphamate" Steroid Biochem. Mol. Biol. 58:611-617 (1996).
Hoshijima et al., "Chronic suppression of heart-failure progression by a pseudophosphorylated mutant of phospholamban via in vivo cardiac rAAV gene delivery" Nat. Med. 8:864-871 (2002).
Hougen & Friedman, "Age-related effects of digoxin on myocardial contractility and Na-K pump in sheep" Am J Physiol. 243(4):H517-22 (1982).
Hulot et al., "Effect of intracoronary administration of AAV1/SERCA2a on ventricular remodelling in patients with advanced systolic heart failure: results from the AGENT-HF randomized phase 2 trial" Eur Heart J 19:1534-1541 (2016).
Iwanaga et al., "Chronic phospholamban inhibition prevents progressive cardiac dysfunction and pathological remodeling after infarction in rats" J Clin Invest 113, 727-736 (2004).
Joffe et al., "Abnormal cardiac function in the streptozolocin-induced non-insulin-dependent diabetic rat: noninvasive assessment with doppler echocardiography and contribution of the nitric oxide pathway" JACC 34(7):2111-2119 (1999).
Johnson et al. "Permeation of steroids through human skin" J. Pharm. Sci. 84:1144-1146 (1995).
Jørgensen, "Purification of Na+,K+-ATPase: enzyme sources, preparative problems, and preparation from mammalian kidney" Methods Enzymol. 156:29-43 (1988).
Kaneko et al., "A pyridone derivative activates SERCA2a by attenuating the inhibitory effect of phospholamban" Eur J Pharmacol 814:1-7 (2017).
Karim et al., "Phosphorylation-dependent conformational switch in spin-labeled phospholamban bound to SERCA" J Mol Biol 358:1032-1040 (2006).
Kaye et al., "Percutaneous cardiac recirculation-mediated gene transfer of an inhibitory phospholamban peptide reverses advanced heart failure in large animals" J. Am. Coll. Cardiol. 50:253-260 (2007).
Lancellotti et al., "European Association of Echocardiography recommendations for the assessment of valvular regurgitation. Part 2: mitral and tricuspid regurgitation (native valve disease)" Eur J Echocardiogr 11(4):307-32 (2010).
Lang et al., "Recommendations for chamber quantification: a report from the American Society of Echocardiography's Guidelines and Standards Commillee and the Chamber Quantification Writing Group, developed in conjunction with the European Association of Echocardiography, a branch of the European Society of Cardiology" J Am Soc Echocardiogr 18(12):1440-63 (2005).
Lipskaya et al., "Sarcoplasmic reticulum Ca(2+) ATPase as a therapeutic target for heart failure" Expert Opin Biol Ther 10:29-41 (2010).
Lloyd-Jones et al., "Lifetime risk for developing congestive heart failure: the Framingham Heart Study" Circulation 106:3068-3072 (2002).
Lohse et al., "What is the role of beta-adrenergic signaling in heart failure?" Circ Res 93:896-906 (2003).
Luciani et al., "Development and physico-chemical characterization of a liposomal formulation of istaroxime" Eur J Pharm Biopharm. 79(2):285-93 (2011).
MacLennan & Kranias, "Phospholamban: a crucial regulator of cardiac contractility" Nat Rev Mol Cell Biol 4(7):566-577 (2003).
Mann & Bristow, "Mechanisms and models in heart failure: the biomechanical model and beyond" Circulation 111:2837-2849 (2005).
Mattera et al., "Istaroxime: a new luso-inotropic agent for heart failure" Am J Cardiol 99(2A):33A-40A (2007).
Metra & Teerlink, "Heart failure" Lancet 390:1981-1995 (2017).
Micheletti et al., "Pharmacological profile of the novel inotropic agent (E,Z)-3-((2-aminoethoxy)imino)androstane-6,17-dione hydrochloride (PST2744)" J Pharmacol Exp Ther 303:592-600 (2002).
Micheletti et al., "Istaroxime, a stimulator of sarcoplasmic reticulum calcium adenosine triphosphatase isoform 2a activity, as a novel therapeutic approach to heart failure" Am J Card 99(2A):24A-32A (2007).
Mihm et al., "Diabetes related cardiomyopathy time dependent echocardiographic evaluation in an experimental rat model" Life Sci. 69(5):527-42 (2001).

(56) References Cited

OTHER PUBLICATIONS

Minamisawa et al., "Chronic phospholamban-sarcoplasmic reticulum calcium ATPase interaction is the critical calcium cycling defect in dilated cardiomyopathy" Cell 99:313-322 (1999).

Mitter et al., "A Test in Context: E/A and E/e' to Assess Diastolic Dysfunction and LV Filling Pressure" JACC 69(11):1451-1464 (2017).

Nagueh et al., "Recommendations for the evaluation of left ventricular diastolic function by echocardiography" Eur J Echocardiogr 10(2):165-93 (2009).

Nakayama et al., "Ca2+- and mitochondrial-dependent cardiomyocyte necrosis as a primary mediator of heart failure" J Clin Invest 117:2431-44 (2007).

Nediani et al., "Stimulation of cardiac sarcoplasmic reticulum calcium pump by acylphosphatase. Relationship to phospholamban phosphorylation" J Biol Chem. 271:19066-73 (1996).

Nicholson & Turner, "Marine steroids. Part III. On the structure of marthasterone glucoside, from the starfish *Marthasterais glacialis*" J. Chem. Soc. Perkin Trans. 1(12):1357-1360 (1976).

No Author listed, "An Account of the Effects of the Digitalis Purpurea in Dropsy" Lond Med J. 6(Pt 1):55-60 (1785).

Ostro & Cullis, "Use of liposomes as injectable-drug delivery systems" Am. J. Hosp. Pharm. 46:1576-1587 (1989).

Packer, "The Room Where It Happens: A Skeptic's Analysis of the New Heart Failure Guidelines" J. Card. Fail. 22:726-730 (2016).

Packer, "Why is the use of digitalis withering? Another reason that we need medical heart failure specialists" Eur J Heart Failure 20:851-852 (2018).

Patel et al., "Hypotension during hospitalization for acute heart failure is independently associated with 30-day mortality: findings from ASCEND-HF" Circ Heart Failure 7:918-925 (2014).

Pellicori et al., "IVC diameter in patients with chronic heart failure: relationships and prognostic significance" JACC Cardiovasc Imaging 6(1):16-28 (2013).

Pinz et al., "Comprimised myocardial energetics in hypertrophied mouse hearts diminish the beneficial effect of overexpressing SERCA2a" J Biol Chem 286(12):10163-10168 (2011).

Revill et al., "Isaroxime" in Drugs of the Future 32(7):595-600 (2007).

Rigopoulus et al., "Acute heart failure. An unmet medical need" Herz44:53-55 (Epub Sep. 22, 2017).

Rocchetti et al., "Modulation of sarcoplasmic reticulum function by Na+/K+ pump inhibitors with different toxicity: digoxin and PST2744 [(E,Z)-3-((2-aminoethoxy)imino)androstane-6,17-dione hydrochloride]" J Pharmacol Exp Ther 313:207-215 (2005).

Sabbah et al., "A canine model of chronic heart failure produced by multiple sequential coronary microembolizations" Am J Physiol. 260:H1379-84 (1991).

Sabbah et al., "Hemodynamic properties of a new-generation positive luso-inotropic agent for the acute treatment of advanced heart failure" Am J Cardiol. 99(2A):41A-46A (2007).

Sato et al., "Rescue of contractile parameters and myocyte hypertrophy in calsequestrin overexpressing myocardium by phospholamban ablation" J Biol Chem 276:9392-99 (2001).

Schwinger et al., "Reduced Ca(2+)-sensitivity of SERCA 2a in falling human myocardium due to reduced serin-16 phospholamban phosphorylation" J Mol Cell Cardiol. 31(3):479-91 (1999).

Seidler et al., "Cyclopiazonic acid is a specific inhibitor of the Ca2+-ATPase of sarcoplasmic reticulum" J Biol Chem. 264:17816-23 (1989).

Shah et al., "Effects of istaroxime on diastolic stiffness in acute heart failure syndromes: results from the Hemodynamic, Echocardiographic, and Neurohormonal Effects of Istaroxime, a Novel Intravenous Inotropic and Lusitropic Agent: a Randomized Controlled Trial in Patients Hospitalized with Heart Failure (HORIZON-HF) trial" Am Heart J 157:1035-41 (2009).

Shattock et al., "Na+/Ca2+ exchange and Na+/K+-ATPase in the heart" J Physiol. 15;593(6):1361-82 (2015).

Solomon et al., "Influence of nonfatal hospitalization for heart failure on subsequent mortality in patients with chronic heart failure" Circulation 116(13):1482-87 (2007).

Tamargo et al. "Investigational Positive Inotropic Agents for Acute Heart Failure" Cardiovasc, & Haematolog, Disorders—Drug Targets 9:193-205 (2009).

Teerlink et al., "Acute Treatment With Omecamtiv Mecarbil to Increase Contractility in Acute Heart Failure: The ATOMIC-AHF Study" J Am Coll Cardiol.67(12):1444-1455 (2016).

Teneggi et al., "Drugs' development in acute heart failure: what went wrong?" Heart Failure Rev 23:667-691 (2018).

ThackerayJT et al., "Sympathetic nervous dysregulation in the absence of systolic left ventricular dysfunction in a rat model of insulin resistance with hyperglycemia" Cardiovasc Diabetol.10(75):1-13 (2011).

Toyoshima et al., "Modeling of the inhibitory interaction of phospholamban with the Ca2+ ATPase" Proc Natl Acad Sci USA 100:467-47 (2003).

Ventura-Clapier et al., "Bloenergetics of the failing heart" Biochim Biophys Acta. 1813(7):1360-72 (2011).

Voelkel et al., "Right ventricular function and failure: report of a National Heart, Lung, and Blood Institute working group on cellular and molecular mechanisms of right heart failure" Circulation 114(17):1883-91 (2006).

Whitbeck et al., "Increased mortality among patients taking digoxin—analysis from the AFFIRM study" Eur Heart J. 34(20):1481-8 (2013).

Zaza & Rocchetti, "Calcium store stability as an antiarrhythmic endpoint" Curr Pharm Des 21:1053-1061 (2015).

Adamson et al., "Hemodynamic effects of a new inotropic compound, PST-2744, in dogs with chronic ischemic heart failure" J Cardiovasc Pharmacol 42:169-173 (2003).

Ambrosy et al., "The global health and economic burden of hospitalizations for heart failure: lessons learned from hospitalized heart failure registries" J Am Coll Cardiol 63:1123-1133 (2014).

Blair et al., "Rationale and Design of the Hemodynamic, Echocardiographic and Neurohormonal Effects of Istaroxime, a Novel Intravenous Inotropic and Lusitropic Agent: A Randomized Controlled Trial in Patients Hospitalized With Heart Failure (HORIZON-HF) Trial" Am. J. Therap. 15(3):231-240 (2008).

Butler et al., "In-hospital worsening heart failure" Eur J Heart Fail 17:1104-1113 (2015).

Carubelli et al., "Treatment with 24 hour istaroxime infusion in patients hospitalised for acute heart failure: a randomized, placebo-controlled trial" Eur J Heart Fail 22:1684-1693 (2020).

Chioncel et al., "Natriuretic peptide-guided management in heart failure" J Cardiovasc Med 17:556-568 (2016).

Chioncel et al., "ESC Heart Failure Long-Term Registry Investigators, Clinical phenotypes and outcome of patients hospitalized for acute heart failure: the ESC Heart Failure Long-Term Registry" Eur J Heart Fail 19:1242-1254 (2017).

Chioncel et al., "ESC-EORP-HFA Heart Failure Long-Term Registry Investigators. Acute heart failure congestion and perfusion status—impact of the clinical classification on in-hospital and long-term outcomes; insights from the ESC-EORP-HFA Heart Failure Long-Term Registry" Eur J Heart Fail 21:1338-1352 (2019).

Chioncel et al., "Istaroxime in acute heart failure: the holy grail is at Horizon?" Eur J Heart Fail. 22(9):1694-1697 (2020).

Database Registry, Compound Registration No. 744195-06-0 (Sep. 14, 2004).

Felker et al., "Heart failure etiology and response to Milrinone in decompensated heart failure. Results from the OPTIME-CHF study" Heart Failure 41(6):997-1003 (2003).

Gheorghiade et al., "OPTIMIZE-HF Investigators and Coordinators, Systolic blood pressure at admission, clinical characteristics, and outcomes in patients hospitalized with acute heart failure" JAMA 296:2217-2226 (2006).

Gheorghiade & Sabbah, "Istaroxime: an investigational luso-inotropic agent for acute heart failure syndromes." Am J Cardiol 99:1A-3A (2007).

(56) References Cited

OTHER PUBLICATIONS

Gheorghiade et al., "Combining SERCA2a activation and Na—K ATPase inhibition: a promising new approach to managing acute heart failure syndromes with low cardiac output" Discov Med 12:141-151 (2011).
Gheorghiade et al., "Current management and future directions for the treatment of patients hospitalized for heart failure with low blood pressure" Heart Fail Rev 18:107-122 (2013).
Hamo et al., "The bumpy road to drug development for acute heart failure" Eur Heart J Suppl 18(Suppl G):G19-G32 (2016).
Harjola et al., "Organ dysfunction, Injury and failure in acute heart failure: from pathophysiology to diagnosis and management. A review on behalf of the Acute Heart Failure Committee of the Heart Failure Association (HFA) of the European Society of Cardiology (ESC)" Eur J Heart Fail 19:821-836 (2017).
Hasenfuss & Teerlink, "Cardiac inotropes: current agents and future directions" Eur Heart J 32:1838-1845 (2011).
Khan et al., "Istaroxime, a first in class new chemical entity exhibiting SERCA-2 activation and Na—K-ATPase inhibition: a new promising treatment for acute heart failure syndromes?" Heart Fail Rev 14:277-287 (2009).
Maack et al., "Treatments targeting inotropy" Eur Heart J 40:3626-3644 (2019).
Mebazaa et al., "Levosimendan vs Dobutamine for patients with acute decompensated heart failure. The survive randomized trial" JAMA 297:1883-1891 (2007).
Mebazaa et al., "Recommendations on pre-hospital & early hospital management of acute heart failure: a consensus paper from the Heart Failure Association of the European Society of Cardiology, the European Society of Emergency Medicine and the Society of Academic Emergency Medicine" Eur J Heart Fail 17: 544-558 (2015).
Mebazaa et al., "ESC Heart Failure Long-Term Registry Investigators. Long-term safety of Intravenous cardiovascular agents in acute heart failure: results from the European Society of Cardiology Heart Failure Long-Term Registry" Eur J Heart Fail 20:332-341 (2018).
Metra et al., "Old and new intravenous inotropic agents in the treatment of advanced heart failure" Prog Cardiovasc Dis 54:97-106 (2011).
Ponikowski et al., "ESC guidelines for the diagnosis and treatment of acute and chronic heart fallure: The Task Force for the diagnosis and treatment of acute and chronic heart failure of the European Society of Cardiology (ESC)" Eur J Heart Fail 18:891-975 (2016).
Psotka et al. "Cardiac calcitropes, myotropes, and mitotropes: JACC review topic of the week" J Am Coll Cardiol 73:2345-2353 (2019).
Teerlink et al., "Agents with inotropic properties for the management of acute heartfailure syndromes. Traditional agents and beyond" Heart Fall Rev 14: 243-253 (2009).
Thackray et al., "The effectiveness and relative effectiveness of intravenous inotropic drugs acting through the adrenergic pathway in patients with heart failure-a meta-regression analysis." Eur J Heart Fail 4:515-529 (2002).
Yancy et al., "ACCF/AHA guideline for the management of heart failure: executive summary: a report of the American College of Cardiology Foundation/American Heart Association Task Force on Practice Guidelines" Circulation 128:1810-1852 (2013).
International Search Report and Written Opinion in international patent application No. PCT/US2022/013278 mailed Apr. 7, 2022.

* cited by examiner

INTRAVENOUS ISTAROXIME FOR THE TREATMENT OF ACUTE HEART FAILURE

CROSS-REFERENCE TO RELATED APPLICATION

This application claims priority to U.S. Provisional Application No. 63/140,552 filed on Jan. 22, 2021, the disclosure of which is incorporated herein by reference.

SUMMARY OF THE INVENTION

Embodiments described herein are directed to methods of treating acute heart failure in a subject in need thereof, comprising administering a therapeutically effective amount of istaroxime or a pharmaceutically acceptable salt, solvate, or hydrate thereof by intravenous infusion over a period of at least 24 hours, wherein the therapeutically effective amount of istaroxime is between about 0.1 μg/kg/min and about 3.0 μg/kg/min; and wherein the subject's acute heart failure is treated.

In some embodiments, the therapeutically effective amount of istaroxime or a pharmaceutically acceptable salt, solvate, or hydrate thereof is about 0.5 μg/kg/min.

In some embodiments, administering a therapeutically effective amount of istaroxime or a pharmaceutically acceptable salt, solvate, or hydrate thereof by intravenous infusion is over a period of at least 24 hours, at least 48 hours, at least 72 hours, or at least 96 hours.

In some embodiments, the subject is a human aged at least 18 years old.

In some embodiments, the subject has at least one of low cardiac output, hypotension, dyspnoea at rest or minimal exertion, need for intravenous diuretic therapy, low systolic blood pressure, hypotension, no signs or symptoms of peripheral hypoperfusion, reduced left ventricular ejection fraction, intermediate to high E/e' ratio, a resting heart rate between about 50 and about 120 beats per minute, brain natriuretic peptide (BNP) levels greater than or equal to 350 pg/mL, N-terminal pro BNP (NT-proBNP) plasma levels greater than or equal to 1400 pg/mL, a potassium level between about 3.8 and about 5.3 mmol/L, and a serum creatinine level greater than 3.0 mg/Dl, or an estimated glomerular filtration rate (eGFR) greater than 30 mL/min/$m^2$ prior to administrating a therapeutically effective amount of istaroxime or a pharmaceutically acceptable salt, solvate, or hydrate thereof. In some embodiments the subject has left ventricular ejection fraction of less than or equal to about 40% of normal. In some embodiments, the subject has an intermediate to high E/e' ratio greater than about 10. In some embodiments, low systolic blood pressure means less than 90 mmHg. In some embodiments, low systolic blood means between about 90 mmHg and about 125 mmHg.

In some embodiments, the subject is hospitalized for acute heart failure, prior to administering a therapeutically effective amount of istaroxime or a pharmaceutically acceptable salt, solvate, or hydrate thereof.

In some embodiments, the subject is not receiving concomitant treatment with intravenous vasodilators, inotropes, vasopressors, oral digoxin or any combination thereof prior to administering a therapeutically effective amount of istaroxime or a pharmaceutically acceptable salt, solvate, or hydrate thereof. In some embodiments, the subject is resistant to diuretics, vasodilators, or a combination thereof.

In some embodiments, administering a therapeutically effective amount of istaroxime or a pharmaceutically acceptable salt, solvate, or hydrate thereof results in a decreased heart rate. In some embodiments, administering a therapeutically effective amount of istaroxime or a pharmaceutically acceptable salt, solvate, or hydrate thereof results in a decreased heart rate by about 3 to about 9 beats per minute.

In some embodiments, administering a therapeutically effective amount of istaroxime or a pharmaceutically acceptable salt, solvate, or hydrate thereof results in an increase in systolic blood pressure. In some embodiments, administering a therapeutically effective amount of istaroxime or a pharmaceutically acceptable salt, solvate, or hydrate thereof results in an increase in systolic blood pressure by about 3 to about 8 mmHg. In some embodiments, administering a therapeutically effective amount of istaroxime or a pharmaceutically acceptable salt, solvate, or hydrate thereof results in an increase in systolic blood pressure by about 15 mmHg.

In some embodiments, administering a therapeutically effective amount of istaroxime or a pharmaceutically acceptable salt, solvate, or hydrate thereof results in an improvement in at least one of cardiac function, hypotension, left ventricular ejection fraction, left ventricular diastolic and systolic function, left ventricular end-systolic and end-diastolic volumes, stroke volume index, E, A, E/A ratio, and S', left atrial dimensions, and inferior vena cava diameter.

In some embodiments, administering a therapeutically effective amount of istaroxime or a pharmaceutically acceptable salt, solvate, or hydrate thereof results in an improvement in cardiac function without tachycardia or hypotension.

In some embodiments, administering a therapeutically effective amount of istaroxime or a pharmaceutically acceptable salt, solvate, or hydrate thereof results in at least one of increased cardiac contractility, increased myocardial relaxation, increased ventricle relaxation, increased rate of myocardial relaxation, increased inotropy, increased left ventricular systolic function, increased stroke volume index, increased afterload associated with decreased E'no", increased renal function, increased organ reperfusion, increased left ventricular ejection fraction, and increased diuresis.

In some embodiments, administering a therapeutically effective amount of istaroxime or a pharmaceutically acceptable salt, solvate, or hydrate thereof results in an increase in renal function.

In some embodiments, administering a therapeutically effective amount of istaroxime or a pharmaceutically acceptable salt, solvate, or hydrate thereof results in a decrease in dyspnoea.

In some embodiments, administering a therapeutically effective amount of istaroxime or a pharmaceutically acceptable salt, solvate, or hydrate thereof does not result in a change in at least one of heart rate, myocardial energy consumption, brain natriuretic peptide (BNP) levels, N-terminal pro BNP (NT-proBNP) levels, and cardiac troponin levels.

In some embodiments, administering a therapeutically effective amount of istaroxime or a pharmaceutically acceptable salt, solvate, or hydrate thereof does not result in at least one of major cardiac adverse events, myocardial ischemia, hypotension, tachycardia, arrhythmias, end organ damage, and increased mortality.

In some embodiments, administering a therapeutically effective amount of istaroxime or a pharmaceutically acceptable salt, solvate, or hydrate thereof does not result in end organ damage. In some embodiments, administering a therapeutically effective amount of istaroxime or a pharmaceutically acceptable salt, solvate, or hydrate thereof does not result in damage to the brain, heart, or kidney.

In some embodiments, administering a therapeutically effective amount of istaroxime or a pharmaceutically acceptable salt, solvate, or hydrate thereof results in an improvement in cardiac function without end organ damage.

In some embodiments, treatment is observable for up to 48 hours, up to 72 hours, or up to 96 hours.

In some embodiments, treatment is observable for at least 48 hours, at least 72 hours, or at least 96 hours.

In some embodiments, administering a therapeutically effective amount of istaroxime or a pharmaceutically acceptable salt, solvate, or hydrate thereof results in a decreased risk of readmissions or emergency visits for cardiovascular reasons for at least 30 days after administration.

In some embodiments, administering a therapeutically effective amount of istaroxime or a pharmaceutically acceptable salt, solvate, or hydrate thereof results in a reduced risk of episodes of in-hospital worsening heart failure for at least 4 days after administration.

In some embodiments, administering a therapeutically effective amount of istaroxime or a pharmaceutically acceptable salt, solvate, or hydrate thereof results in a reduced length of stay, reduced post-discharge adverse events, reduced subject readmissions or any combination thereof.

Some embodiments further comprise a downward titration of istaroxime or a pharmaceutically acceptable salt, solvate, or hydrate thereof following intravenous infusion over a period of at least 24 hours. In some embodiments, a downward titration involves a decrease in the rate of infusion of istaroxime or a pharmaceutically acceptable salt, solvate, or hydrate thereof.

Some embodiments further comprise administering a diuretic. Some embodiments further comprise administering at least 20 mg intravenous furosemide. Some embodiments further comprise administering at least 40 mg intravenous furosemide.

Some embodiments further comprise administering an antiemetic if the subject experiences gastrointestinal upset.

In some embodiments, administering a therapeutically effective amount of istaroxime or a pharmaceutically acceptable salt, solvate, or hydrate thereof replaces treatment with beta-blockers, mineralocorticoid receptor antagonists, angiotensin receptor II blockers, ACE inhibitors, digitalis, diuretics, vasodilators, inotropes, vasopressors, oral digoxin, or any combination thereof prior to administering a therapeutically effective amount of istaroxime or a pharmaceutically acceptable salt, solvate, or hydrate thereof.

Some embodiments are directed to administering a metabolite of istaroxime to an subject with acute heart failure comprising administering istaroxime or a pharmaceutically acceptable salt, solvate, or hydrate thereof by intravenous infusion over a period of at least 24 hours wherein the amount of istaroxime is between about 0.1 μg/kg/min and about 3.0 μg/kg/min; and wherein the subject's acute heart failure is treated.

In some embodiments, administering istaroxime or a pharmaceutically acceptable salt, solvate, or hydrate thereof by intravenous infusion is for a duration sufficient to produce a therapeutically effective amount of an istaroxime metabolite. In some embodiments, a therapeutically effective amount of an istaroxime metabolite is a plasma level of the istaroxime metabolite that is greater than about 5 ng/ml. In some embodiments, a therapeutically effective amount of an istaroxime metabolite is a plasma level of the istaroxime metabolite that is greater than about 20 ng/ml. In some embodiments, a therapeutically effective amount of an istaroxime metabolite is a plasma level of the istaroxime metabolite that between about 20 ng/ml and about 25 ng/ml. In some embodiments, administering istaroxime or a pharmaceutically acceptable salt, solvate, or hydrate thereof by intravenous infusion is for a duration sufficient of at least about 24 hours. In some embodiments, the istaroxime metabolites may comprise a compound of formula (II) or formula (III):

Formula (II)

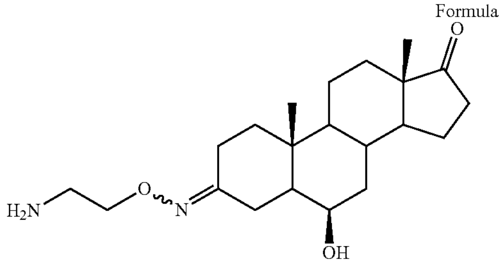

PST 2915

Formula (III)

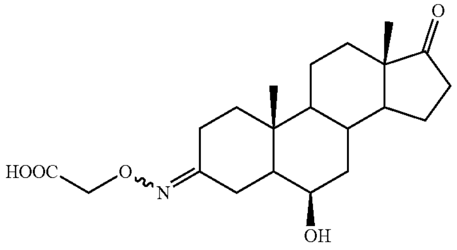

PST 3093

In some embodiments, the metabolite is PST 2915 (Formula II), PST 3093 (Formula (III) or a combination thereof, and the subject is Caucasian. In some embodiments, the metabolite is PST 2915 (Formula II), PST 3093 (Formula (III), or a combination thereof, and the subject is Asian.

Some embodiments are directed to a pharmaceutical composition comprising a therapeutically effective amount of istaroxime or a pharmaceutically acceptable salt, solvate, or hydrate thereof for intravenous infusion over a period of about 24 hours, wherein the therapeutically effective amount of istaroxime or a pharmaceutically acceptable salt, solvate, or hydrate thereof is sufficient to administer between about 0.1 μg/kg/min and about 3.0 μg/kg/min of istaroxime or a pharmaceutically acceptable salt, solvate, or hydrate thereof over about 24 hours.

DETAILED DESCRIPTION OF THE INVENTION

Figure 1:
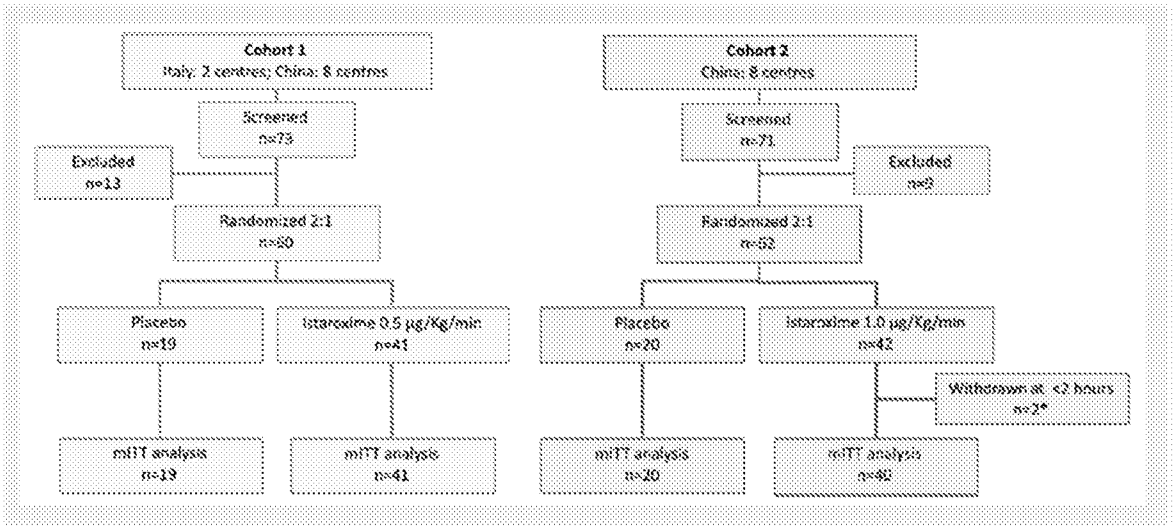
FIG. 1 depicts patient disposition (Consort plot. mITT, modified intention-to-treat: *Exclusion of patients from mITT analysis was pre-specified in the study protocol).

Unless defined otherwise, all technical and scientific terms used herein have the same meaning as those commonly understood by one of ordinary skill in the art to which this invention belongs. Standard techniques are used unless otherwise specified. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

As used herein, the singular forms "a," "an," and "the" include the plural referents unless the context clearly indicates otherwise.

The term "about" refers to the variation in the numerical value of a measurement, e.g. used to obtain that measure. In one embodiment, the term "about" means within 10% of the reported numerical value.

The term "heart failure" or "HF" refers to a clinical syndrome characterized by typical symptoms (e.g. dyspnoea, ankle swelling and fatigue) that may be accompanied by signs (e.g. elevated jugular venous pressure, pulmonary crackles and peripheral edema) caused by a structural and/or functional cardiac abnormality, resulting in a reduced cardiac output and/or elevated intracardiac pressures at rest or during stress.

The terms "acute heart failure" or "AHF" are used interchangeably herein and refer generally to a rapid onset or worsening of symptoms and/or signs of HF requiring immediate treatment and hospitalization. The current definition of "acute heart failure" is rather nonspecific and may include a broad spectrum of conditions with several phenotypes characterized by different clinical presentation, etiology, precipitating factors, therapeutic approach, and prognosis. In addition, a large proportion of patients have a subacute course of the disease with a progressive worsening of signs and symptoms of HF which could develop days before hospital admission.

The terms "chronic heart failure" or "CHF" are used interchangeably herein and refer to the current clinical classification of chronic HF based on the presence of signs and symptoms of HF and left ventricular ejection fraction (LVEF), recognizing three categories: "heart failure with reduced ejection fraction" or "HFrEF," which is characterized by an LVEF of less than about 40%; "heart failure with mid-range ejection fraction" or "HFmEF" or "HFmrEF," which is characterized by an LVEF from about 40% to about 49%; and "heart failure with preserved ejection fraction" or "FIFpEF," which is characterized by an LVEF of equal to or greater than about 50%. The terms "HFmEF" and "HFpEF" include two additional criteria, namely increased natriuretic peptides levels (BNP>35 pg/ml and/or NT-proBNP>125 pg/mL) associated with the evidence of structural and/or functional heart disease (left ventricular hypertrophy and/or left atrium enlargement and/or evidence of diastolic dysfunction).

The term "treating" refers to any indicia of success in the treatment or amelioration of the disease or condition. Treating can include, for example, reducing or alleviating the severity of one or more symptoms of the disease or condition, or it can include reducing the frequency with which symptoms of a disease, defect, disorder, or adverse condition, and the like, are experienced by a subject. In some embodiments, "treating" may include reducing or alleviating the severity of one or more symptoms of the disease or condition, or it can include reducing the frequency with which symptoms of a disease, defect, disorder, or adverse condition, and the like, are experienced by a subject for a defined period of time after administration of istaroxime. In yet other embodiments, "treating" may include reducing or alleviating the severity of one or more symptoms of the disease or condition, or it can include reducing the frequency with which symptoms of a disease, defect, disorder, or adverse condition, and the like, are experienced by a subject such that the subject can be discharged from hospital and resume chronic therapy for the disease, defect, disorder, or adverse condition or in some cases may cease one or more chronic therapy for the disease, defect, disorder, or adverse condition.

The term "preventing" refers to the prevention of the disease or condition in a subject. For example, if a subject at risk of developing heart failure is treated with the methods of the present invention and does not later develop heart failure, then the disease has been prevented in that subject. In some embodiments, "preventing" may also refer to the prevention of a particular symptoms or consequences of the disease or condition. For example, if a subject at risk of developing one or more symptoms or consequences of heart failure is treated with the methods of the present invention and does not later develop the particular symptom or consequence, then the symptom of consequence has been prevented in that subject.

The term "treat or prevent" is sometimes used herein to refer to a method that results in some level of treatment or amelioration of the disease or condition, and contemplates a range of results directed to that end, including but not restricted to prevention of the disease or condition entirely or a particular symptom or consequence of the disease or condition.

As used herein, the term "pharmaceutically acceptable carrier" means a chemical composition with which istaroxime or a pharmaceutically acceptable salt, solvate, or hydrate thereof, or a metabolite of istaroxime may be combined and which, following the combination, can be used to administer the compound to a subject.

As used herein, the term "pharmaceutically acceptable" salt, solvate, hydrate, or ester means a salt, solvate, hydrate, or ester form of the active ingredient which is compatible with any other ingredients of the pharmaceutical composition, which is not deleterious to the subject to which the composition is to be administered.

The term "intravenous infusion" refers to the administration or delivery of liquid substances directly into a vein of a mammal. Typical "infusions" use only the pressure supplied by gravity.

The term "parameter" as used herein to refer to measuring heart function and means any heart function that is observable or measurable using suitable measuring techniques available in the art. A non-limiting list of exemplary "parameters" of heart function include heart rate, blood pressure, diastolic relaxation, systolic contraction, LVEF, diastolic blood pressure, systolic blood pressure, cardiac output, stroke volume, deceleration slope, cardiac index, mitral inflow velocity, and the like. As one having ordinary skill in the art will appreciate, measuring one or more "parameters" of heart function can be used to detect heart failure in a subject and can also be used to determine whether heart function has improved, or if the acute heart failure has been treated following or during treatment.

The terms "therapeutically active" or "active" ingredient or compound refer to a substance that provides a beneficial effect to the individual to whom the substance is administered.

A "therapeutically effective amount" is the amount of a composition or active ingredient sufficient to provide a beneficial effect to the individual to whom the composition or active ingredient is administered. In some embodiments, A "therapeutically effective amount" is the amount of a composition or active ingredient sufficient to treat and/or prevent the disease or condition or a symptom or consequence of the disease or condition.

Acute heart failure (AHF) is a complex clinical syndrome requiring hospitalization for urgent therapy and represents a significant burden to the healthcare system (Ambrosy A P, Fonarow G C, Butler J, Chioncel O, Greene S J, Vaduganathan M, Nodari S, Lam C S, Sato N, Shah A N, Gheorghiade M. The global health and economic burden of hospitalizations for heart failure: lessons learned from hospitalized heart failure registries. J Am Coll Cardiol 2014:63:1123-1133). Heart failure is responsible for more than 1 million hospitalizations per year both in Europe and in America (Ambrosy et al.) In addition, patients with AHF have a high 1-year mortality rate (25-30%) and experience multiple readmissions (Chioncel O, Mebazaa A, Harjola V P, Coats A J, Piepoli M F, Crespo-Leiro M G, Laroche C, Seferovic P M, Anker S D, Ferrari R, Ruschitzka F, Lopez-Fernandez S, Miani D, Filippatos G, Maggioni A P: ESC Heart Failure Long-Term Registry Investigators. Clinical phenotypes and outcome of patients hospitalized for acute heart failure: the ESC Heart Failure Long-Term Registry. Eur J Heart Fail 2017:19:1242-1254). Despite improving the initial signs and symptoms of AHF during hospitalization, current intravenous therapies have failed to reduce post-discharge event rates, and in some cases, may contribute to increased morbidity and mortality (Hamo C E, Butler J, Gheorghiade M, Chioncel O. The bumpy road to drug development for acute heart failure. Eur Heart J Suppl 2016:18(Suppl G):G19-G32). Most AHF patients are treated with diuretics and vasodilators to alleviate congestion, while others may also receive inotropes and/or vasopressors. In AHF, inotropes are required for the treatment of the subset of patients with low cardiac output and resultant symptomatic hypotension and/or end-organ hypoperfusion (Ponikowski P, Voors A A, Anker S D, Bueno H, Cleland J G, Coats A J, Falk V, Gonzalez-Juanatey J R, Harjola V P, Jankowska E A, Jessup M, Linde C, Nihoyannopoulos P, Parissis J T, Pieske B, Riley J P, Rosano G M, Ruilope L M, Ruschitzka F, Rutten F H, van der Meer P. 2016 ESC guidelines for the diagnosis and treatment of acute and chronic heart failure: The Task Force for the diagnosis and treatment of acute and chronic heart failure of the European Society of Cardiology (ESC). Developed with the special contribution of the Heart Failure Association (HFA) of the ESC. Eur J Heart Fail 2016:18:891-975). Overall, inotropes were used in 12% of patients admitted with AHF enrolled in the European Society of Cardiology Heart Failure Long-Term Registry, with higher proportions in those presenting with the 'wet and cold' profile (28%) (Chioncel O, Mebazaa A, Maggioni A P, Harjola V P, Rosano G, Laroche C, Piepoli M F, Crespo-Leiro M G, Lainscak M, Ponikowski P, Filippatos G, Ruschitzka F, Seferovic P, Coats A J S, Lund L H: ESC-EORP-HFA Heart Failure Long-Term Registry Investigators. Acute heart failure congestion and perfusion status-impact of the clinical classification on in-hospital and long-term outcomes: insights from the ESC-EORP-HFA Heart Failure Long-Term Registry. Eur J Heart Fail 2019:21:1338-1352) or in those presenting with cardiogenic shock (81%) (Hamo et al.). Inappropriate use as well as increasing short- and long-term safety concerns have been reported regarding the use of inotropes and/or vasopressors in AHF. Clinical data collected on the effects of catecholamines, phosphodiesterase inhibitors and calcium sensitizers indicate an overall increase in mortality relative to usual care. Possible explanations for the increased mortality include increased myocardial oxygen consumption and a heightened propensity for cardiac arrhythmias. In addition, the vasodilator properties may lead to hypotension, reduce coronary perfusion pressure, and predispose to arrhythmias (Thackray S, Easthaugh J, Freemantle N, Cleland J G. The effectiveness and relative effectiveness of intravenous inotropic drugs acting through the adrenergic pathway in patients with heart failure—a meta-regression analysis. Eur J Heart Fail 2002:4:515-529; Felker G M, Benza R L, Chandler A B, Leimberger J D, Cuffe M S, Califf R M, Gheorghiade M, O'Connor C M; OPTIME-CHF Investigators. Heart failure etiology and response to milrinone in decompensated heart failure: results from the OP-TIME-CHF study. J Am Coll Cardiol 2003:41:997-1003; Mebazaa A, Nieminen M S, Packer M, Cohen-Solal A, Kleber F X, Pocock S J, Thakkar R, Padley R J, Põder P, Kivikko M: SURVIVE Investigators. Levosimendan vs dobutamine for patients with acute decompensated heart failure: the SURVIVE randomized trial. JAMA 2007:297:1883-1891: Packer M, Colucci W, Fisher L, Massie B M, Teerlink J R, Young J, Padley R J, Thakkar R, Delgado-Herrera L, Salon J, Garratt C, Huang B, Sarapohja T: REVIVE Heart Failure Study Group. Effect of levosimendan on the short-term clinical course of patients with acutely decompensated heart failure. JACC Heart Fail 2013:1:103-111; Khan H, Metra M, Blair J E, Vogel M, Harinstein M E, Filippatos G S, Sabbah H N, Porchet H, Valentini G, Gheorghiade M. Istaroxime, a first in class new chemical entity exhibiting SERCA-2 activation and Na-K-ATPase inhibition: a new promising treatment for acute heart failure syndromes? Heart Fail Rev 2009; 14:277-287). Given the lack of clear efficacy and the increase in mortality associated with existing inotropic agents used in AHF, there is a critical need for the development of inotropic therapy that relieves symptoms rapidly but does not increase mortality risk.

Istaroxime is a novel pharmacologic agent with both inotropic and lusitropic properties and holds promise for the very difficult to treat high-risk patients with AHF presenting with low blood pressure (Gheorghiade M, Blair J E, Filippatos G S, Macarie C, Ruzyllo W, Korewicki J, Bubenek-Turconi S I, Ceracchi M, Bianchetti M, Carminati P, Kremastinos D, Valentini G, Sabbah H N: HORIZON-HF Investigators. Hemodynamic, echocardiographic, and neurohormonal effects of istaroxime, a novel intravenous inotropic and lusitropic agent: a randomized controlled trial in patients hospitalized with heart failure. J Am Coll Cardiol 2008:51:2276-2285). The inotropic effects of istaroxime are due to its ability to inhibit sodium-potassium adenosine triphosphate (Na-KATPase), leading to an increase in cytosolic calcium concentration and thus improved contractility. The lusitropic effects are related to its ability to stimulate sarcoplasmic reticulum calcium ATPase isoform 2 (SERCA2), leading to rapid sequestration of cytosolic calcium back into the sarcoplasmic reticulum during diastole and thereby promoting myocardial relaxation (Khan et al.). The greater calcium uptake in the sarcoplasmic reticulum allows increased release of calcium during systole, thereby increasing contractility. Results from animal experiments with istaroxime validate this favorable mechanistic profile by showing increased inotropy and accelerated relaxation without associated increased energy consumption or arrhythmias (Khan et al.). In an animal heart failure model, a direct comparison of istaroxime and dobutamine suggests the change in dP/dtmax during treatment was similar between the two agents, but peak heart rate was significantly lower with istaroxime (Adamson P B, Vanoli E, Mattera G G, Germany R, Gagnol J P, Carminati P, Schwartz P J. Hemodynamic effects of a new inotropic compound, PST-2744, in dogs with chronic ischemic heart failure. J Cardiovasc Pharmacol 2003:42:169-173). Furthermore, using tissue Doppler, istaroxime improved myocardial relaxation (assessed by e' diastolic velocity), when compared to dobutamine (Adamson et al.).

In the HORIZON-HF (Hemodynamic, Echocardiographic, and Neurohormonal Effects of Istaroxime, a Novel Intravenous Inotropic and Lusitropic Agent: a Randomized Controlled Trial in Patients Hospitalized with Heart Failure) trial, 120 AHF patients with systolic blood pressure (SBP) of 90-150 mmHg were randomized 3:1 to receive istaroxime or placebo. Istaroxime was administered at 0.5, 1.0, and 1.5 μg/kg/min for 6 h, and serial haemodynamic assessments were performed (Gheorghiade et al.). All three doses of istaroxime lowered pulmonary capillary wedge pressure, the primary study endpoint, by 3 to 5 mmHg compared with placebo.

However, cardiac index increased only at the highest dose. The study confirmed prior animal studies that showed a significant decline in heart rate and shortening of the QTc interval (−29 to −49 ms) during treatment (Khan et al.) A favorable lusitropic effect, as assessed by increased mitral deceleration time, occurred only at the highest dose (Shah S J, Blair J E, Filippatos G S, Macarie C, Ruzyllo W, Korewicki J, Bubenek-Turconi S I, Ceracchi M, Bianchetti M, Carminati P, Kremastinos D, Grzybowski J, Valentini G, Sabbah H N, Gheorghiade M: HORIZON-HF Investigators. Effects of istaroxime on diastolic stiffness in acute heart failure syndromes: results from the Hemodynamic, Echocardiographic, and Neurohormonal Effects of Istaroxime, a Novel Intravenous Inotropic and Lusitropic Agent: A Randomized Controlled Trial in Patients Hospitalized with Heart Failure (HORIZON-HF) trial. Am Heart J 2009; 157: 1035-1041). Carubelli et al. (Carubelli V, Zhang Y, Metra M, Lombardi C, Felker G M, Filippatos G, O'Connor C M, Teerlink J R, Simmons P, Segal R, Malfatto G, La Rovere M T, Li D, Han X, Yuan Z, Yao Y, Li B, Lau L F, Bianchi G, Zhang J; Istaroxime ADHF Trial Group. Treatment with 24 hour istaroxime infusion in patients hospitalised for acute heart failure: a randomized, placebo-controlled trial. Eur J Heart Fail 2020 Jan. 23) evaluated the effects of a 24 h infusion of two doses of istaroxime in patients hospitalized for AHF with left ventricular ejection fraction (LVEF)≤40%. The study was a randomized, double-blind, placebo-controlled, parallel-group study, designed to evaluate the efficacy of two different doses of istaroxime (0.5 and 1.0 μg/kg/min) as compared to placebo. A total of 96 patients from China and 24 from Italy were randomly assigned to one of two doses of istaroxime or placebo delivered as an intravenous infusion over 24 h in a 2:1 ratio within two sequential cohorts of 60 patients each. Inclusion criteria included an ongoing hospitalization for AHF with dyspnoea at rest or on minimal exertion and need for intravenous diuretic therapy (>40 mg intravenous furosemide); SBP between 90 and 125 mmHg without signs or symptoms of peripheral hypoperfusion: intermediate to high E/e' ratio by tissue Doppler echocardiography (>10); B-type natriuretic peptide (BNP) or N-terminal pro-BNP (NT-proBNP) plasma levels ≥350 pg/mL or ≥1400 pg/mL, respectively. The primary efficacy endpoint was the change from baseline to 24 h after the start of the infusion in the E/e' ratio. In the intention-to-treat analysis, the mean change in E/e' ratio at 24 h was −4.55 (4.75) in the istaroxime 0.5 μg/kg/min group vs. −1.55 (4.11) in the placebo cohort 1 group (P=0.029) and −3.16 (2.59) in the istaroxime 1.0 μg/kg/min group vs. −1.08 (2.72) in the placebo cohort 2 group (P=0.009). Both istaroxime doses significantly increased stroke volume index compared with placebo, though the increase in LVEF did not reach statistical significance. There was a decrease in heart rate and an increase in SBP, which reached statistical significance with the 1.0 μg/kg/min dose. A favorable effect on renal function was observed with istaroxime, with an increase in the estimated glomerular filtration rate (eGFR) in the high dose group compared with placebo at 24 h. Self-reported dyspnoeaand NT-proBNP changes showed no significant differences between istaroxime and placebo. Absolute troponin levels were not different with istaroxime treatment compared with placebo, and no major untoward effects, including arrhythmias were observed. The rate of serious adverse events did not show any significant differences in the three arms, although a numerical higher number was observed in the istaroxime 1.0 μg/kg/min group (n=6, 15%). Adverse drug reactions, particularly gastrointestinal events, were more common with istaroxime treatment. The main efficacy result was the ability of a 24 h infusion of istaroxime to improve diastolic and systolic function parameters. While the changes were similar at both doses tested and better than placebo, these effects were seen without an increase in heart rate, unlike traditional inotropes. A sustained increase in SBP was observed with both doses of drug, reaching significance with the higher istaroxime dose. The results are comparable to those observed in the HORIZON-HF study, (Gheorghiade et al.) and the trend of E/e' decrease parallels the trend in decrease in pulmonary capillary wedge pressure. Although other inotropes improve cardiac performance to a similar or greater extent than istaroxime, the main difference with this agent is the effect on blood pressure, heart rate and diastolic function. The fact that istaroxime caused a decrease in E/e' while simultaneously increasing SBP is remarkable, given that increased afterload has previously been associated with decreased E'. An intriguing point is the absence of any association between NT-proBNP changes and treatment with istaroxime, association seen with most of the therapies able to improve cardiac performance (Chioncel O, Collins S P, Greene S J, Ambrosy A P, Vaduganathan M, Macarie C, Butler J, Gheorghiade M. Natriuretic peptide-guided management in heart failure. J Cardiovasc Med 2016:17:556-568). Future research studies, with larger sample size and/or longer duration of istaroxime infusion should elucidate this finding. End-organ damage, injury and subsequent dysfunction of target organs (i.e. heart, kidneys, liver) in the setting of AHF has been associated with increased risk for mortality (Harjola V P, Mullens W, Banaszewski M, Bauersachs J, Brunner-La Rocca H P, Chioncel O, Collins S P, Doehner W, Filippatos G S, Flammer A, Fuhrmann V, Lainscak M, Lassus J, Legrand M, Masip J, Mueller C, Papp Z, Parissis J, Platz E, Rudiger A, Ruschitzka F, Schäfer A, Seferovic P M, Skouri H, Yilmaz M B, Mebazaa A. Organ dysfunction, injury and failure in acute heart failure: from pathophysiology to diagnosis and management. A review on behalf of the Acute Heart Failure Committee of the Heart Failure Association (HFA) of the European Society of Cardiology (ESC). Eur J Heart Fail 2017:19:821-836). In the present study, there were no differences in troponin release after study drug infusion in either the istaroxime or placebo group (Carubelli et al.). These findings suggest that istaroxime-induced improvements in diastolic function do not increase myocardial oxygen demand or increase myocardial damage. Along with improvement in renal function (increased eGFR), these effects suggest better organ protection, making the drug a potentially attractive option for the treatment of patients with hypotension and low cardiac output. The pharmacokinetic profile may also be beneficial in critically ill patients. With a very rapid onset of action and rapid washout after infusion termination (60 min half-time), this drug may be suitable for the use in critically ill patients. While istaroxime appears promising, future studies should look at infusion times longer than 24 h to prevent the abrupt reversal of the beneficial changes in vital signs (increase in heart rate and decrease in SBP) and echocardiographic parameters (increase in E/e' and decrease in stroke volume index)(Carubelli et al.). This suggests a pronounced 'rebound' phenomenon, and may require a gradual discontinuation of istaroxime infusion rate.

This study is now the second positive randomized controlled trial investigating the effect of istaroxime infusion in patients with AHF and reduced LVEF. In contrast to other available inotropic agents, the beneficial haemodynamic changes are associated with a reduction in heart rate and increases in SBP. In light of these properties, istaroxime appears to be a promising agent for patients presenting with AHF, particularly those with low SBP due to reduced cardiac output. However, further research is required to determine when istaroxime should be initiated and for what duration of time in this subset of AHF patients. Randomized studies of longer infusions of istaroxime, and comparing istaroxime with other available inotropic agents in patients with low cardiac output will further confirm the efficacy and safety profile of this therapy. Finally, larger studies will need to test the efficacy of istaroxime on post-discharge clinical outcomes such as AHF readmission and mortality in patients with borderline SBP or low cardiac output. (Chioncel O, Collins S P, Butler J. Istaroxime in acute heart failure: the holy grail is at HORIZON? Eur J Heart Fail. 2020 September; 22(9): 1694-1697).

Embodiments described herein are directed to methods of treating acute heart failure in a subject in need thereof, comprising administering a therapeutically effective amount of istaroxime or a pharmaceutically acceptable salt, solvate, or hydrate thereof by intravenous infusion over a period of at least 24 hours, wherein the therapeutically effective amount of istaroxime is between about 0.1 μg/kg/min and about 3.0 μg/kg/min; and wherein the subject's acute heart failure is treated.

Istaroxime is an inotropic compound having the following structural formula (I):

Formula (I)

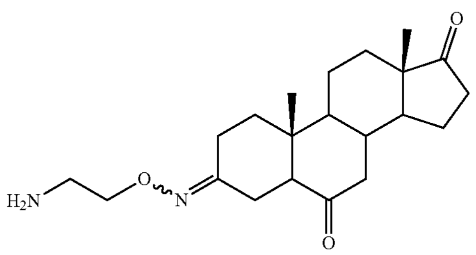

or a pharmaceutically acceptable salt, solvate, or hydrate thereof.

Upon administering to a subject such as a human, istaroxime is metabolized into several metabolites that are capable of activating SERCA2a. The istaroxime metabolic pathway is illustrated below:

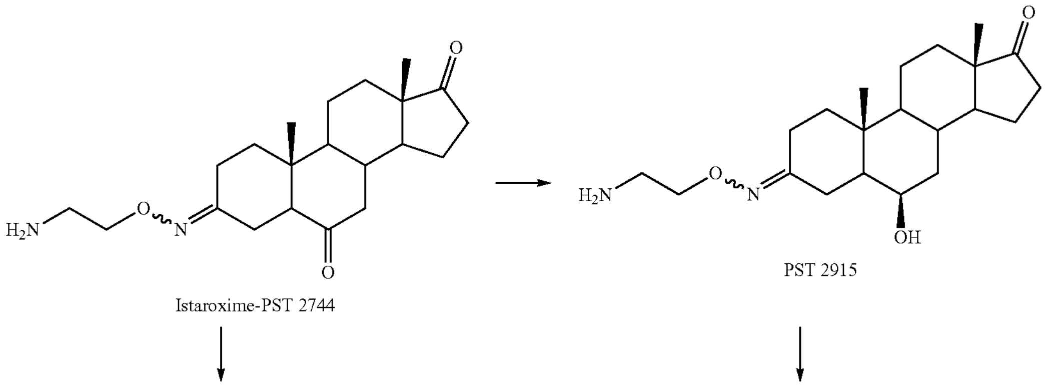

Istaroxime-PST 2744

PST 2915

-continued

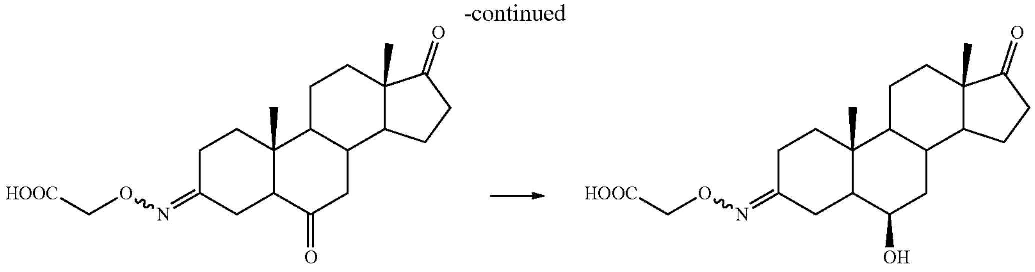

PST 2922 PST 3093

As such, disclosed herein are metabolites of istaroxime having SERCA2a activity that have the following structural formulas (II) and (III):

Formula (II)

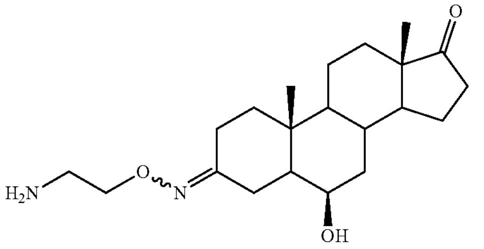

PST 2915

Formula (III)

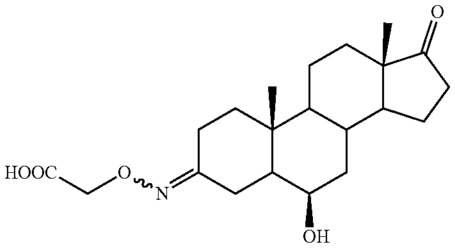

PST 3093

In some embodiments, the metabolite of istaroxime (PST 3093) is endowed with selective or "pure" SERCA2a activity is the compound of formula (III).

In some embodiments, the therapeutically effective amount of istaroxime or a pharmaceutically acceptable salt, solvate, or hydrate thereof is about 0.5 μg/kg/min. In yet other embodiments, a therapeutically effective amount of istaroxime or an equivalent of a pharmaceutically acceptable salt, solvate, or hydrate thereof is from about 0.1 μg/Kg/min to about 3.0 μg/Kg/min, e.g., 0.1 μg/Kg/min, 0.15 μg/Kg/min, 0.2 g/Kg/min, 0.25 μg/Kg/min, 0.3 μg/Kg/min, 0.35 μg/Kg/min, 0.4 μg/Kg/min, 0.5 μg/Kg/min, 0.6 μg/Kg/min, 0.7 μg/Kg/min, 0.8 μg/Kg/min, 0.9 μg/Kg/min, 1.0 μg/Kg/min, 1.1 μg/Kg/min, 1.2 μg/Kg/min, 1.3 μg/Kg/min, 1.4 μg/Kg/min, 1.5 μg/Kg/min, 1.6 μg/Kg/min, 1.7 μg/Kg/min, 1.8 μg/Kg/min, 1.9 μg/Kg/min, 2.0 μg/Kg/min, 2.1 μg/Kg/min, 2.2 μg/Kg/min, 2.3 μg/Kg/min, 2.4 μg/Kg/min, 2.5 μg/Kg/min, 2.6 μg/Kg/min, 2.7 μg/Kg/min, 2.8 μg/Kg/min, 2.9 μg/Kg/min, or 3.0 μg/Kg/min.

In some embodiments, the administering a therapeutically effective amount of istaroxime or a pharmaceutically acceptable salt, solvate, or hydrate thereof by intravenous infusion is over a period of at least 24 hours, at least 48 hours, at least 72 hours, or at least 96 hours.

In some embodiments, the subject is a human aged at least 18 years old.

Gap Intentional?

In some embodiments, the subject has at least one of low cardiac output, hypotension, dyspnoea at rest or minimal exertion, need for intravenous diuretic therapy, low systolic blood pressure, hypotension, no signs or symptoms of peripheral hypoperfusion, reduced left ventricular ejection fraction, intermediate to high E/e ratio, a resting heart rate between about 50 and about 120 beats per minute, brain natriuretic peptide (BNP) levels greater than or equal to 350 pg/mL, N-terminal pro BNP (NT-proBNP) plasma levels greater than or equal to 1400 pg/mL, a potassium level between about 3.8 and about 5.3 mmol/L, and a serum creatinine level greater than 3.0 mg/dL or an estimated glomerular filtration rate (eGFR) greater than 30 $mL/min/m^2$ prior to administrating a therapeutically effective amount of istaroxime or a pharmaceutically acceptable salt, solvate, or hydrate thereof. In some embodiments the subject has left ventricular ejection fraction of less than or equal to about 40% of normal. In some embodiments, the subject has an intermediate to high E/e' ratio greater than about 10. In some embodiments, low systolic blood pressure means less than 90 mmHg. In some embodiments, low systolic blood means between about 90 mmHg and about 125 mmHg.

In some embodiments, the subject is hospitalized for acute heart failure, prior to administering a therapeutically effective amount of istaroxime or a pharmaceutically acceptable salt, solvate, or hydrate thereof.

In some embodiments, the subject is not receiving concomitant treatment with intravenous vasodilators, inotropes, vasopressors, oral digoxin or any combination thereof prior to administering a therapeutically effective amount of istaroxime or a pharmaceutically acceptable salt, solvate, or hydrate thereof.

In some embodiments, the subject is resistant to diuretics, vasodilators, or a combination thereof.

In some embodiments, administering a therapeutically effective amount of istaroxime or a pharmaceutically acceptable salt, solvate, or hydrate thereof results in a decreased heart rate. In some embodiments, administering a therapeutically effective amount of istaroxime or a pharmaceutically acceptable salt, solvate, or hydrate thereof results in a decreased heart rate by about 3 to about 9 beats per minute.

In some embodiments, administering a therapeutically effective amount of istaroxime or a pharmaceutically acceptable salt, solvate, or hydrate thereof results in an increase in systolic blood pressure. In some embodiments, administering a therapeutically effective amount of istaroxime or a pharmaceutically acceptable salt, solvate, or hydrate thereof results in an increase in systolic blood pressure by about 3 to about 8 mmHg. In some embodiments, administering a therapeutically effective amount of istaroxime or a pharmaceutically acceptable salt, solvate, or hydrate thereof results in an increase in systolic blood pressure by about 15 mmHg.

In some embodiments, administering a therapeutically effective amount of istaroxime or a pharmaceutically acceptable salt, solvate, or hydrate thereof results in an improvement in at least one of cardiac function, hypotension, left ventricular ejection fraction, left ventricular diastolic and systolic function, left ventricular end-systolic and end-diastolic volumes, stroke volume index, E, A, E/A ratio, and S', left atrial dimensions, and inferior vena cava diameter.

In some embodiments, administering a therapeutically effective amount of istaroxime or a pharmaceutically acceptable salt, solvate, or hydrate thereof results in an improvement in cardiac function without tachycardia or hypotension.

In some embodiments, administering a therapeutically effective amount of istaroxime or a pharmaceutically acceptable salt, solvate, or hydrate thereof results in at least one of increased cardiac contractility, increased myocardial relaxation, increased ventricle relaxation, increased rate of myocardial relaxation, increased inotropy, increased left ventricular systolic function, increased stroke volume index, increased afterload associated with decreased E'no", increased renal function, increased organ reperfusion, increased left ventricular ejection fraction, and increased diuresis.

In some embodiments, administering a therapeutically effective amount of istaroxime or a pharmaceutically acceptable salt, solvate, or hydrate thereof results in an increase in renal function.

In some embodiments, administering a therapeutically effective amount of istaroxime or a pharmaceutically acceptable salt, solvate, or hydrate thereof results in a decrease in dyspnoea.

In some embodiments, administering a therapeutically effective amount of istaroxime or a pharmaceutically acceptable salt, solvate, or hydrate thereof does not result in a change in at least one of heart rate, myocardial energy consumption, brain natriuretic peptide (BNP) levels, N-terminal pro BNP (NT-proBNP) levels, and cardiac troponin levels.

In some embodiments, administering a therapeutically effective amount of istaroxime or a pharmaceutically acceptable salt, solvate, or hydrate thereof does not result in at least one of major cardiac adverse events, myocardial ischemia, hypotension, tachycardia, arrhythmias, end organ damage, and increased mortality.

In some embodiments, administering a therapeutically effective amount of istaroxime or a pharmaceutically acceptable salt, solvate, or hydrate thereof does not result in end organ damage. In some embodiments, administering a therapeutically effective amount of istaroxime or a pharmaceutically acceptable salt, solvate, or hydrate thereof does not result in damage to the brain, heart, or kidney.

In some embodiments, administering a therapeutically effective amount of istaroxime or a pharmaceutically acceptable salt, solvate, or hydrate thereof results in an improvement in cardiac function without end organ damage.

In some embodiments, treatment is observable for up to about 48 hours, up to about 72 hours, or up to about 96 hours. In some embodiments, treatment is observable for up to about 48 hours, up to about 72 hours, or up to about 96 hours from the start of the infusion with istaroxime. In some embodiments, treatment is observable for up to about 48 hours, up to about 72 hours, or up to about 96 hours following cessation of the infusion with istaroxime.

In some embodiments, treatment is observable for at least 48 hours, at least 72 hours, or at least 96 hours. In some embodiments, treatment is observable for at least 48 hours, at least 72 hours, or at least 96 hours from the start of the infusion with istaroxime. In some embodiments, treatment is observable for at least 48 hours, at least 72 hours, or at least 96 hours following cessation of the infusion with istaroxime.

In some embodiments, administering a therapeutically effective amount of istaroxime or a pharmaceutically acceptable salt, solvate, or hydrate thereof results in a decreased risk of readmissions or emergency visits for cardiovascular reasons for at least 30 days after administration. In some embodiments, administering a therapeutically effective amount of istaroxime or a pharmaceutically acceptable salt, solvate, or hydrate thereof results in a decreased risk of readmissions or emergency visits for cardiovascular reasons for at least 30 days after cessation of the infusion with istaroxime.

In some embodiments, administering a therapeutically effective amount of istaroxime or a pharmaceutically acceptable salt, solvate, or hydrate thereof results in a reduced risk of episodes of in-hospital worsening heart failure for at least 4 days after administration. In some embodiments, administering a therapeutically effective amount of istaroxime or a pharmaceutically acceptable salt, solvate, or hydrate thereof results in a reduced risk of episodes of in-hospital worsening heart failure for at least 4 days after cessation of the infusion of istaroxime.

In some embodiments, administering a therapeutically effective amount of istaroxime or a pharmaceutically acceptable salt, solvate, or hydrate thereof results in a reduced length of stay, reduced post discharge adverse events, reduced subject readmissions or any combination thereof.

Some embodiments further comprise a downward titration of istaroxime or a pharmaceutically acceptable salt, solvate, or hydrate thereof following intravenous infusion over a period of at least 24 hours. In some embodiments, a downward titration involves a decrease in the rate of infusion of istaroxime or a pharmaceutically acceptable salt, solvate, or hydrate thereof. For example, a decrease in the rate of infusion may be from about 1 μg/kg/min to about 0.5 μg/kg/min or from about 0.5 μg/kg/min to about 0.25 μg/kg/min. In some embodiments, a downward titration is initiated following observation that the subject is successfully treated. In yet other embodiments, a downward titration is initiated at a specific time point after the initiation of infusion, for example, in a non-limiting example, for a 24 hour infusion, a downward titration may be initiated at about 20 hours. In yet other embodiments, a downward titration can be initiated in response to an adverse effect of administering istaroxime or a pharmaceutically acceptable salt, solvate, or hydrate thereof.

Some embodiments further comprise administering a diuretic. Some embodiments further comprise administering at least 20 mg intravenous furosemide. Some embodiments further comprise administering at least 40 mg intravenous furosemide.

Some embodiments further comprise administering an antiemetic if the subject experiences gastrointestinal upset.

In some embodiments, administering a therapeutically effective amount of istaroxime or a pharmaceutically acceptable salt, solvate, or hydrate thereof replaces treatment with beta-blockers, mineralocorticoid receptor antagonists, angiotensin receptor II blockers, ACE inhibitors, digitalis, diuretics, vasodilators, inotropes, vasopressors, oral digoxin or any combination thereof prior to administering a therapeutically effective amount of istaroxime or a pharmaceutically acceptable salt, solvate, or hydrate thereof.

In some embodiments, administering a therapeutically effective amount of istaroxime or a pharmaceutically acceptable salt, solvate, or hydrate thereof may further comprise administering existing and future drug classes and/or specific drugs such as: a) drug classes such as, ACE inhibitors, Angiotensin II receptor blockers (ARBs), diuretics, Ca channel blockers, beta blockers, digitalis, NO donors, vasodilators, SERCA2a stimulators, neprilysin (NEP) inhibitors, myosin filament activators, recombinant relaxin-2 mediators, recombinant NP protein, activators of the soluble Guanylate Cyclase (sGC), beta-arrestin ligand of Angiotensin II receptor, aldosterone antagonists, Angiotensin receptor/neprilysin inhibitor (ARNI), nitrates, non-dihydropyridines, or anticoagulants; and b) specific drugs: hydrochlorothyzide, furosemide, bumetanide, torasemide, verapamil, diltiazem, carvedilol, metoprolol, hydralazine, eplerenone, spironolactone, lisinopril, ramipril, nitroglycerin, nitrates, digoxin, valsartan, olmesartan, telmisartan, candesartan, losartan, entresto, omecamtiv, sacubitril, serelaxin, ularitide, levosimendan, cinaciguat, metolazone, chlorthalidone, lisinopril, ramipril, sacubitril, carvedilol, metoprolol hydralazine, isosorbide dinitrate, nitroglycerin, amlodipine, felodipine, diltiazem, verapamil, or ivabradine.

In some embodiments, combination therapy can be carried out by administering istaroxime both at the same time or at different times than one or more additional therapeutic agents. In case of concomitant administration, the compound of the present invention and the additional therapeutic agent can be each formulated in a separate pharmaceutical compositions or in the same unitary dosage form. In the former case, the present invention provides a kit, in particular for the treatment of acute heart failure, comprising separate pharmaceutical compositions containing istaroxime and the additional therapeutic agent, respectively. In another embodiment, the present invention provides a pharmaceutical unit dosage form kit, in particular for the treatment of acute heart failure, comprising istaroxime and the additional therapeutic agent in the same unit dosage form. Combination therapy according to the present invention may be used in the treatment of acute heart failure potentially due to the inotropic-lusitropic effect of istaroxime in addition to or synergistically combined with the therapeutic effect of the additional active agents herein disclosed.

In some embodiments, administration of istaroxime or a pharmaceutically acceptable salt, solvate, or hydrate thereof allows for the accumulation of one or more of its metabolites, at least one of which exhibits single function SERCA2a activation (i.e., behaves as a "pure" SERCA2a activator). The compositions and methods disclosed herein will be described in more detail below. Some embodiments are directed to administering a metabolite of istaroxime to a subject with acute heart failure comprising administering a therapeutically effective amount of istaroxime or a pharmaceutically acceptable salt, solvate, or hydrate thereof by intravenous infusion over a period of at least 24 hours wherein the therapeutically effective amount of istaroxime is between about 0.5 μg/kg/min and about 3.0 μg/kg/min; and wherein the subject's acute heart failure is treated.

In some embodiments, administering istaroxime or a pharmaceutically acceptable salt, solvate, or hydrate thereof by intravenous infusion is for a duration sufficient to produce a therapeutically effective amount of an istaroxime metabolite. In some embodiments, a therapeutically effective amount of an istaroxime metabolite is a plasma level of the istaroxime metabolite that is greater than about 5 ng/ml. In some embodiments, a therapeutically effective amount of an istaroxime metabolite is a plasma level of the istaroxime metabolite that is greater than about 20 ng/ml. In some embodiments, a therapeutically effective amount of an istaroxime metabolite is a plasma level of the istaroxime metabolite between about 20 ng/ml and 25 ng/ml. In some embodiments, administering istaroxime or a pharmaceutically acceptable salt, solvate, or hydrate thereof by intravenous infusion is for a duration sufficient of at least about 24 hours. In particular, the istaroxime metabolites may comprise a formula (II) or a formula (III) compound, such as:

Formula (II)

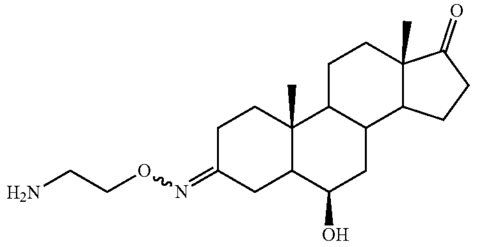

PST 2915

Formula (III)

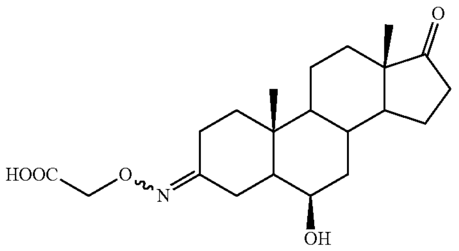

PST 3093

In some embodiments, the metabolite is PST 2915 (Formula II), PST 3093 (Formula (III) or a combination thereof and the subject is Caucasian.

In some embodiments, the metabolite is PST 2915 (Formula II), PST 3093 (Formula (III), or a combination thereof and the subject is Asian.

Some embodiments are directed to a pharmaceutical composition comprising a therapeutically effective amount of istaroxime or a pharmaceutically acceptable salt, solvate, or hydrate thereof for intravenous infusion over a period of about 24 hours; wherein the therapeutically effective amount of istaroxime or a pharmaceutically acceptable salt, solvate, or hydrate thereof is sufficient to administer between about 0.5 μg/kg/min and about 3.0 μg/kg/min of istaroxime or a pharmaceutically acceptable salt, solvate, or hydrate thereof over about 24 hours.

The measurement of one or more cardiac parameters disclosed herein can be measured by Echocardiography which may be performed on subjects according to international standards (see, for example, Lang R M et a I. J Am Soc Echocardiogr 2005; 18(12): 1440-63; Nagueh S F et al. Eur J Echocardiogr 2009; 10(2): 165-93; Evangelista A et a I. Eur J Echocardiogr 2008; 9(4):438-48).

In some embodiments, cardiac parameters can be measured as follows:

1. Cardiac dimension measures:
   a. Left ventricle end diastolic diameter (EDD): measured with M-mode echocardiography at the level of mitral valve (MV) leaflets from parasternal long axis view (PLAX) (normal range [N R]: 42-59 mm males and 39-53 mm females);
   b. Left ventricle end systolic diameter (ESD): measured with M-mode echocardiography at the level of mitral valve (MV) leaflets from PLAX (N R: 25-35 mm):
   c. Left ventricle end diastolic volume (EDV): measured with M-mode echocardiography at the level of mitral valve (MV) leaflets from PLAX (N R: 67-155 mL males and 56-104 mL females);
   d. Left ventricle end systolic volume (ESV): measured with M-mode echocardiography at the level of mitral valve (MV) leaflets from PLAX (N R: 22-58 mL males and 19-49 mL females);
   e. Left atrium diameter (LAD): measured at end-ventricular systole with M-mode echocardiography from PLAX. (N R: 30-40 mm males and 27-38 mm females)
   f. Left atrium area (LAA): measured from apical four chamber view (NR: £20 cm2); and
   g. Left atrium volume (LAV): derived from area-length measured from apical four chamber view (N R: 18-58 mL males and 22-52 mL females).
2. Left ventricle diastolic function parameters:
   a. E wave: measured from mitral valve pulsed wave Doppler, is the peak velocity of early filling. Normal range for all the diastolic parameters significantly changes with age;
   b. A wave: measured from mitral valve pulsed wave Doppler is the peak velocity of late atrial filling. Not evaluable in subjects with AF:
   c. E wave deceleration time (EDT): measured from mitral valve pulsed wave Doppler represent the slope of the descending part of E wave;
   d. E/A ratio: determines the type of diastolic filling pattern (normal E/A=1-2 and EDT=150-200 ms, abnormal relaxation E/A<1 and EDT>240 ms, pseudonormal E/A=0.8-1.5: restrictive E/A$^3$2 and EDT <160 ms). Not evaluable in subjects with AF;
   e. Ea: measured with tissue Doppler method at the lateral and septal side of the mitral annulus from apical four chamber view is the early diastolic velocity. The value has been calculated as the average between Ea lateral and Ea septal. (NR310 cm/s) (see Nagueh S F et al. Eur J Echocardiogr. 2009:10(2): 165-93);
   f. Aa: measured with tissue Doppler method at the lateral and septal side of the mitral annulus from apical four chamber view is the late atrial diastolic velocity. The value has been calculated as the average between Aa lateral and Aa septal. Not evaluable in subjects with AF; and
   g. E/Ea ratio: this is a derived measure from E and Ea value. This is highly correlated with left ventricle filling pressure and with prognosis in subjects with HF. (NR: <13) (see Nagueh S F et al. supra).
3. Left ventricle systolic function parameters:
   a. Left ventricle ejection fraction (LVEF): measured with Simpson biplane method according to international recommendations from apical four chamber view and apical two chamber view. (NR $^3$55%) (see Lang R M et al. J Am Soc Echocardiogr. 2005:18 (12): 1440-63); and
   b. Sa: measured with tissue Doppler method at the lateral and septal side of the mitral annulus from apical four chamber view. The value has been calculated as the average between Sa lateral and Sa septal. Validation studies demonstrated that Sa correlates with LVEF (NR $^3$6 cm/s) (see Gulati V K et al. Am J Cardiol. 1996:77(11):979-84).
4. Overall cardiac contraction parameters:
   a. Stroke volume (SV): is a derived measure obtained with the application of Bernoulli's formula using the dimension of left ventricle outflow tract (LVOT) as diameter and LVOT time velocity integral as velocity. (NR>60 mL/beat);
   b. Cardiac output (CO): is derived by the multiplication of SV× heart rate (HR) (NR: >4 L/min);
   c. Stroke volume index (SVI): is a derived parameter obtained by the adjustment of SV by body surface area (BSA) (NR: 33-47 mL/beat/m$^2$); and
   d. Cardiac index (CI): is a derived parameter obtained by the adjustment of CO by body surface area (BSA) (NR: 2.5-4 L/min/m$^2$).
5. Right ventricle function parameters:
   a. Pulmonary arterial systolic pressure (PASP): estimated by the sum of the peak velocity at tricuspidal continuous wave Doppler and a fixed value derived from inferior vena cava diameter and respiratory change. (NR<35 mmHg);
   b. Tricuspid annular plane systolic excursion (TAPSE): measured from M-mode echocardiography from apical four chamber view. TAPSE correlates with right ventricle ejection fraction and its reduction associated with worse prognosis in HF. (NR>16 mm) (see Ghio S et al J Am Coll Cardiol 2001; 37(1): 183-8); and
   c. Right ventricle Sa: measured with tissue Doppler method at right ventricle free wall from apical four chamber view. Sa is a derived parameter of systolic function and correlated with right ventricle ejection fraction. (NR>10 cm/s) (see Voelkel N F et al. Circulation 2006; 114(17): 1883-91: Haddad F et al. Circulation 2008; 117(13): 1717-31).
6. Other parameters:
   a. Mitral regurgitation (MR): evaluated with a visual qualitative assessment and graded in four categories: none, mild, moderate, and severe (see Lancellotti P et al. Eur J Echocardiogr 2010:11(4): 307-32); and
   b. Inferior vena cava diameter (IVC): measured with M-mode echocardiography from subcostal view at 1-2 cm from the junction with right atrium. This parameter has been used to estimate systolic pulmonary artery pressure. It correlated with right atrium pressure indicating the grade of congestion. Increased IVC diameter is associated with prognosis in subjects with HF (NR: <1.5 cm) (see Pellicori P et al. JACC Cardiovasc Imaging 2013:6(1): 16-28; Voelkel N F et al. Circulation 2006:114(17): 1883-91).

In some embodiments, quantitative measurements relating to PST 2744 and its metabolite PST 2915 may be obtained by HPLC-MS/MS including a mobile phase of 70:30 acetonitrile/water, 1 mL/L IM formic acid, and 1 mL/L 5M ammonium acetate. The flow rate is 1 mL/min, and the chromatographic separation is by reversed phase HPLC (Column: SYNERGI 4m POLAR-RP80A 150×4.6 mm equipped with a Security-guard Phenomenex Polar-RP 4×3 mm). Detection may be performed by MS/MS, and the acquisition mode may be by Multiple Reaction Monitoring (MRM).

In some embodiments, quantitative measurements relating to PST 2922 and PST 3093 in human plasma may also be measured by the HPLC-MS/MS method. The mobile phase was 50:50 H2 0/CH3 CN (v/v) and 500 mL/L 98-100% HCOOH. The flow rate was 1 mL/min and chromatographic separation was done by reversed-phase HPLC (Column: Phenomenex Phenyl hexyl, 150×4.6 mm, equipped with a Phenomenex phenyl propyl guard-cartridge) under isocratic conditions. Detection was performed by MS/MS (376.0 282.0 amu for PST2922, 378.0 284.0 amu for PST 3093 and 362.0 268.0 amu for PST 3418, IS).

The pharmaceutical compositions and formulations for intravenous infusion described herein can be formulated in any way and can be administered in a variety of unit dosage forms depending upon the condition or disease and the degree of illness, the general medical condition of each subject, the resulting preferred method of administration and the like. Details on techniques for formulation and administration are well described in the scientific and patent literature, see, e.g., the latest edition of Remington's Pharmaceutical Sciences, Mack Publishing Co, Easton PA ("Remington's").

The formulations may conveniently be presented in unit dosage form and may be prepared by any method known in the art of pharmacy. The amount of active ingredient which can be combined with a carrier or vehicle material to produce a single dosage form will vary depending upon the subject being treated and the particular mode of administration. The amount of active ingredient that can be combined with a carrier material to produce a single dosage form will generally be the amount of the compound which produces a therapeutic effect.

Pharmaceutical formulations as provided herein can be prepared according to any method known to the art for the manufacture of pharmaceuticals. Such formulations can contain additional agents, such as preserving or stabilizing agents. A formulation can be admixtured with nontoxic pharmaceutically acceptable carriers or excipients which are suitable for manufacture. Formulations may comprise one or more diluents, emulsifiers, preservatives, buffers, excipients, etc. and may be provided in such forms as liquids, powders, emulsions, lyophilized powders, etc.

Aqueous suspensions can contain an active agent (e.g., a composition used to practice the uses and methods as provided herein) in admixture with excipients suitable for the manufacture of aqueous suspensions. Such excipients include a suspending agent, such as sodium carboxymethylcellulose, methylcellulose, hydroxypropyl-methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate. Formulations can be adjusted for osmolarity.

According to the present invention, istaroxime is given by intravenous (IV) administration. These formulations can comprise a solution of active agent dissolved in a pharmaceutically acceptable carrier. Acceptable vehicles and solvents that can be employed are water, dextrose in water, and Ringer's solution, an isotonic sodium chloride. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the subject's needs. The administration is by bolus or continuous infusion (e.g., substantially uninterrupted introduction into a blood vessel for a specified period of time).

Istaroxime as provided herein can be lyophilized. Provided herein is a stable lyophilized formulation comprising a composition as provided herein, which can be made by lyophilizing a solution comprising a pharmaceutical as provided herein and a bulking agent, e.g. mannitol, trehalose, raffinose, and sucrose or mixtures thereof. There are many other conventional lyophilizing agents. Among the sugars, lactose is the most common. Also used are citric acid, sodium carbonate, EDTA, Benzyl alcohol, glycine, sodium chloride, etc. (see, for example, Journal of Excipients and Food Chemistry Vol. 1, Issue 1 (2010) pp 41-54: U.S. patent app. no. 20040028670). In a preferred embodiment, istaroxime or a pharmaceutically acceptable salt, solvate, or hydrate thereof can be prepared as powder for injection according to the teaching of CN 103315968.

According to the present invention, istaroxime or a pharmaceutically acceptable salt, solvate, or hydrate thereof as provided herein can be administered for prophylactic and/or therapeutic treatments. In therapeutic applications, compositions are administered to a subject already suffering from a condition, or disease in an amount sufficient to treat, prevent, cure, alleviate or partially arrest the clinical manifestations of the condition, or disease and its complications (i.e. a "therapeutically effective amount"). For example, in alternative embodiments, pharmaceutical compositions as provided herein are administered in an amount sufficient to treat, prevent or ameliorate in an individual in need thereof. The amount of pharmaceutical composition adequate to accomplish this is defined as a "therapeutically effective dose." The dosage schedule and amounts effective for this use, i. e., the "dosing regimen," will depend upon a variety of factors, including the stage of the disease or condition, the severity of the disease or condition, the general state of the subject's health, the subject's physical status, age and the like. In calculating the dosage regimen for a subject, the mode of administration also is taken into consideration.

Single or multiple administrations of the formulations disclosed herein can be given depending on the dosage and frequency as required by the AHF clinical symptoms of subject. The formulations disclosed herein provide a sufficient quantity of active agent to effectively treat or prevent or ameliorate a conditions, diseases or symptoms as described herein.

Also provided herein are methods of treating a subject with acute heart failure. In preferred embodiments, the individual exhibits symptoms of, or has been diagnosed with, acute heart failure.

In general, the compositions described herein can be used to treat the individual having heart failure or acute heart failure. In an embodiment, the method of therapy includes providing or presenting the individual having heart failure or acute heart failure. In some cases, a measuring step is first carried out to determine the baseline heart function of the individual. For instance, an individual with heart failure may exhibit impaired or decreased diastolic relaxation function. The measuring step may include measuring one or more parameters of heart failure, such as, but not limited to, decreased heart rate, decreased heart pressure, decreased systolic and/or diastolic blood pressure, reduced left ventricular end-diastolic/systolic volume and function (LVEF), or increased E/Ea or E/A ratios reduced Ea ratio decreased stroke volume. In some embodiments, the measuring step may comprise measuring on or more of cardiac function, cardiac output, hypotension, dyspnoea, systolic blood pressure, signs or symptoms of peripheral hypoperfusion, left ventricular ejection fraction, systolic function, E/e ratio, resting heart rate, heart rate, brain natriuretic peptide (BNP) levels, N-terminal pro BNP (NT-proBNP) plasma levels, cardiac troponin levels, potassium level serum creatinine level or estimated glomerular filtration rate (eGFR), left ventricular end-systolic and end-diastolic volumes, stroke volume index, E, A, E/A ratio, and S', left atrial dimensions, inferior vena cava diameter, tachycardia, cardiac contractility, myocardial relaxation, ventricle relaxation, rate of myocardial relaxation, inotropy, left ventricular systolic function, stroke volume index, afterload associated with decreased E'no", renal function, organ reperfusion, end organ damage, or diuresis before, during, or after administration of istaroxime. As one having ordinary skill in the art will appreciate, any suitable measuring technique available in the art at the time of the measuring step is suitable for use herein, and it is well within the purview of such skilled artisan to select an appropriate measuring technique corresponding to the parameter of interest. A non-limiting list of suitable measuring equipment/techniques includes echocardiogram, cardiac catheterization, nuclear stress test, CAT scan, radionuclide ventriculography scan, stethoscope, sphygmomanometer, and the like. For instance, the diastolic relaxation can be measured by echocardiography or PCWP.

The methods disclosed herein also include administering to the individual a therapeutically effective amount of istaroxime or a metabolite thereof, such as PST 3093. In preferred embodiments, the istaroxime or istaroxime metabolite is in a pharmaceutical composition, such as any one of the combinations discussed above. The istaroxime or istaroxime metabolite is administered in a dose as disclosed elsewhere herein, e.g., between about 0.25 mg/Kg/min to about 1.0 mg/Kg/min. In some embodiments, the route of administration is infusion, such as intravenous fusion. The measuring step can be performed before, during, or after the administering step. For instance, it may be desired to continually monitor one or more of the parameters of heart function disclosed herein during treatment and for a period of time thereafter.

As discussed above, it has been surprisingly discovered that administering istaroxime (or its metabolites) by infusion for an infusion duration of at least 24 hours results in increased SERCA2a activity and improving diastolic relaxation without causing arrhythmogenic effects due to, for example, $Na^+/K^+$ pump inhibition. In this manner, istaroxime infusion of at least 24 hours exerts a lusitropic-SERCA2a activity that is prevailing on the inotropic activity and results in improved diastolic relaxation.

While not intending to be bound by theory, it is believed that this later-arising "pure" SERCA2a activation is due to an accumulation of istaroxime metabolites in the plasma of the individual. As such, in some embodiments, istaroxime is administered via intravenous infusion for a period of time sufficient to enable the accumulation of istaroxime metabolites in the plasma of the individual. In preferred embodiments, the infusion duration is sufficient to allow for the accumulation of one or more istaroxime metabolites: preferably, the metabolite is PST 2915 having the structural formula (II) or PST 3093 having the structural formula (III): more preferably, the metabolite is PST 3093. In some embodiments, the accumulation of istaroxime metabolite in the plasma is at a concentration of least about 3 ng/mL, e.g., 3 ng/mL, 4 ng/mL, 5 ng/mL, 6 ng/mL, 7 ng/ml, 8 ng/mL, 9 ng/ml, 10 ng/ml, 11 ng/ml, 12 ng/mL, 13 ng/mL, 14 ng/ml, 15 ng/ml, 16 ng/mL, 17 ng/ml, 18 ng/mL, 19 ng/mL, 20 ng/mL, 21 ng/ml, 22 ng/ml, 23 ng/mL, 24 ng/ml, 25 ng/ml, 26 ng/mL, 27 ng/ml, 28 ng/ml, 29 ng/mL, 30 ng/mL, 35 ng/mL, 40 ng/ml, 45 ng/mL, 50 ng/ml or more for a period of time of at least about 24 h. In one embodiment, the istaroxime metabolite accumulates in the plasma to the desired concentration within 24 hours of istaroxime infusion initiation and is maintained at or above that concentration for at least about 24 additional hours. In some embodiments, the desired plasma concentration of metabolite is at least about 5 ng/mL.

As one having ordinary skill in the art would appreciate, the plasma concentration of istaroxime or istaroxime metabolites can be measured by conventional means, such as by HPLC-MS/MS.

The following example further illustrates the present invention.

Example 1-Treatment with 24 Hour Istaroxime Infusion in Patients Hospitalized for Acute Heart Failure: A Randomized, Placebo-Controlled Trial Abstract Istaroxime is a first-in-class agent which acts through inhibition of the sarcolemma Na+/K+ pump and activation of the SERCA2a pump. This study assessed the effects of a 24 h infusion of istaroxime in patients hospitalized for acute heart failure (AHF). We included patients hospitalized for AHF with left ventricular ejection fraction ≤40% and E/e' >10. Patients were randomized to a 24 h intravenous infusion of placebo or istaroxime at doses of 0.5 μg/kg/min (cohort 1: placebo n=19; istaroxime n=41) or 1.0 μg/kg/min (cohort 2: placebo n=20, istaroxime n=40). The primary endpoint of change in E/e ratio from baseline to 24 h decreased with istaroxime vs. placebo (cohort 1: −4.55±4.75 istaroxime 0.5 μg/kg/min vs. −1.55±4.11 placebo, P=0.029; cohort 2: −3.16±2.59 istaroxime 1.0 g/kg/min vs. −1.08±2.72 placebo, P=0.009). Both istaroxime doses significantly increased stroke volume index and decreased heart rate. Systolic blood pressure increased with istaroxime, achieving significance with the high dose. Self-reported dyspnoea and N-terminal pro-brain natriuretic peptide improved in all groups without significant differences between istaroxime and placebo. No significant differences in cardiac troponin absolute values or clinically relevant arrhythmias were observed during or after istaroxime infusion. Serious cardiac adverse events (including arrhythmias and hypotension) did not differ between placebo and istaroxime groups. The most common adverse events were injection site reactions and gastrointestinal events, the latter primarily with istaroxime 1.0 μg/kg/min.

Introduction

Despite the overwhelming epidemiological, clinical, and economic burden, the natural history of acute heart failure (AHF) has remained unchanged over recent decades. Within the AHF population, patients presenting with low systolic blood pressure (SBP) are a high-risk group with unfavorable outcomes. No evidence based, safe treatment has emerged for this subgroup and current therapy is still based on traditional inotropic agents, which are associated with untoward effects, including tachycardia, arrhythmias, myocardial ischemia, hypotension, and increased mortality. Many of these adverse cardiac events are mediated by an increase in cytosolic calcium concentrations, worsened by the depression of sarcoplasmic reticulum calcium adenosine triphosphatase isoform 2a (SERCA2a) activity that occurs in heart failure. Hypotension is caused by concomitant vascular effects of many inotropic agents and may further deteriorate tissue hypoperfusion.

Figure 4:
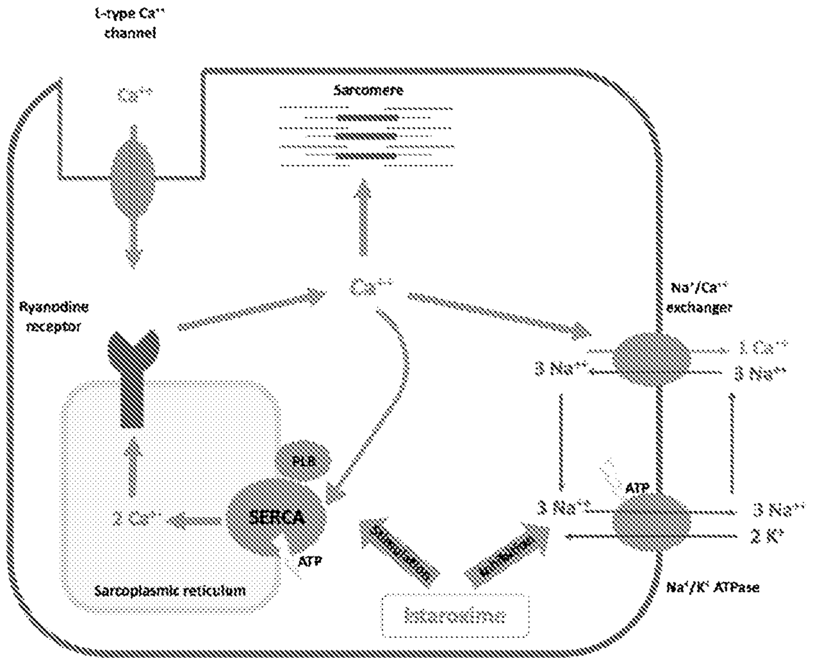
FIG. 4 depicts the putative istaroxime mechanism of action.

Istaroxime is a first-in-class agent with a dual mechanism of action involving the inhibition of the sarcolemmal Na+/K+ pump and the activation of the SERCA2a pump activity (FIG. 4). This is mediated by the displacement of phospholamban from SERCA2a causing enhanced calcium reuptake by the sarcoplasmic reticulum, independently of intracellular cyclic AMP concentrations. Reduced cytoplasmic free calcium levels during diastole improve relaxation and result in increased calcium release during systole, enhancing cardiac contractility. In a phase II trial in patients with worsening heart failure and reduced left ventricular systolic function (HORIZON-HF), a 6 h istaroxime infusion resulted in improvements of both left ventricular diastolic and systolic function, with a slight increase in SBP and reduction in heart rate (HR). These effects support a potential therapeutic role for istaroxime in the treatment of patients with AHF and reduced left ventricular ejection fraction (LVEF) since improvements in cardiac function without tachycardia or hypotension differentiate this agent from traditional inotropes. We designed a clinical trial to assess the effects of a prolonged istaroxime infusion of 24 h in patients hospitalized for AHF with reduced LVEF and low SBP.

Methods

This study was a phase II, multicenter, randomized, double-blind, placebo-controlled, parallel group investigation, conducted at two sites in Italy and eight sites in China. All patients provided written informed consent. The study was approved by country regulatory authorities and by local institutional review boards. The trial is registered in the European Clinical Trials Database (EudraCT 2013-000540-26) and ClinicalTrials.gov (NCT02617446).

Study Population

Patients were randomized 2:1 to istaroxime or placebo 24 h infusion and were enrolled in two sequential cohorts, the first with an istaroxime dose of 0.5 μg/kg/min and the second with an istaroxime dose of 1.0 μg/kg/min. At the end of cohort 1 enrollment, an independent Data Safety and Monitoring Board conducted an interim safety analysis of unblinded data before proceeding to cohort 2 enrollment. Inclusion criteria were: age ≥18 years, an ongoing hospitalization for AHF with dyspnoea at rest or minimal exertion and need for intravenous diuretic therapy (40 mg intravenous furosemide), SBP between 90 and 125 mmHg without signs or symptoms of peripheral hypoperfusion: LVEF ≤40%: intermediate to high E/e' ratio by tissue Doppler echocardiography (10); brain natriuretic peptide (BNP) or N-terminal pro BNP (NT-proBNP) plasma levels ≥350 pg/mL or ≥1400 pg/mL, respectively, and presence of adequate echocardiographic windows. The main exclusion criteria were: concomitant or planned treatment with intravenous vasodilators, inotropes or vasopressors: treatment with oral digoxin (patients treated with digoxin within the last week could be randomized if the plasma concentration at screening was 0.5 ng/mL); acute coronary syndrome or stroke within the past 3 months: coronary artery bypass graft or percutaneous coronary intervention within the past month or planned in the next month: resting HR >120 bpm or <50 bpm: life-threatening ventricular arrhythmia or implantable cardioverter-defibrillator shock within the past month: fever 38° C.; serum creatinine 3.0 mg/dL or estimated glomerular filtration rate (eGFR) 30 mL/min/m2; serum potassium 5.3 mmol/L or 3.8 mmol/L; severe hepatic dysfunction.

Clinical Endpoints

The primary efficacy endpoint was the change from baseline to 24 h after the start of the infusion in the E/e ratio assessed by tissue Doppler echocardiography. Secondary endpoints included the change from baseline to 24 h of other echocardiography parameters: LVEF, left ventricular end-systolic and end-diastolic volumes, stroke volume index, E, A, E/A ratio, and S': changes in dyspnoea by visual analogue scale (VAS) and in NT-proBNP from baseline to 24 h: proportion of patients with hospital readmissions or emergency visits for cardiovascular reasons by day 30; proportion of patients with episodes of in-hospital worsening heart failure to day 4, and length of stay. In-hospital worsening heart failure was defined by the need to increase the dose or reinitiate intravenous therapy with diuretics and/or other inotropic agents to day 4. Safety endpoints were assessed throughout the study and included: incidence of adverse events (AEs): change in vital signs and in 12-lead electrocardiographic (ECG) parameters: incidence of clinically or haemodynamically significant episodes of supraventricular or ventricular arrhythmias detected by continuous ECG monitoring: standard laboratory parameters: renal function: cardiac troponin T (cTnT): incidence of cTnT elevations, and mortality at day 30. Elevations in cTnT were considered significant if they were >50% or >20% from baseline values, for patients with cTnT below or above the 99% upper reference limit at baseline, respectively.

Study Procedures

Figure 5:
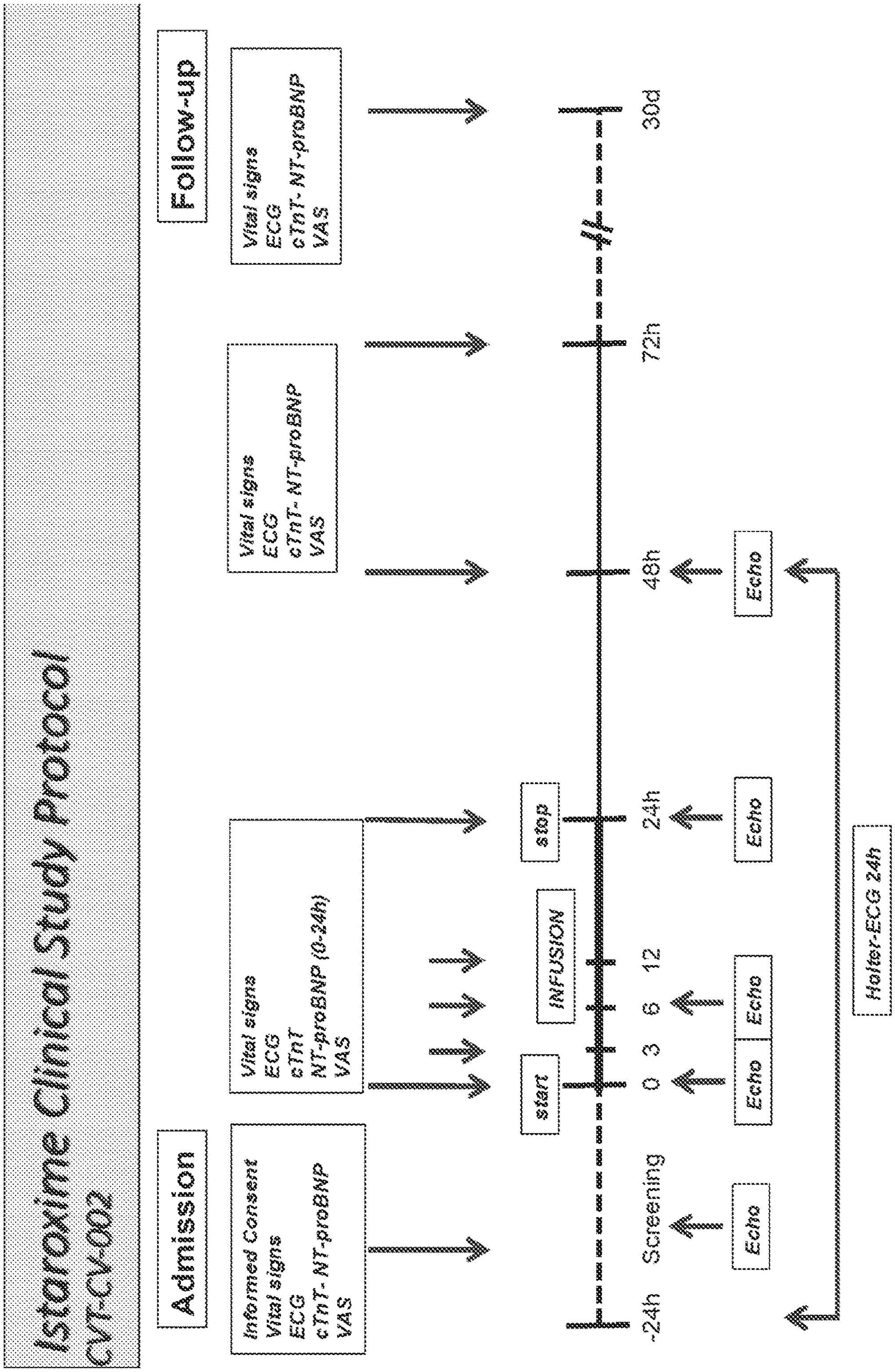
FIG. 5 depicts the study flow-chart.
Figure 6:
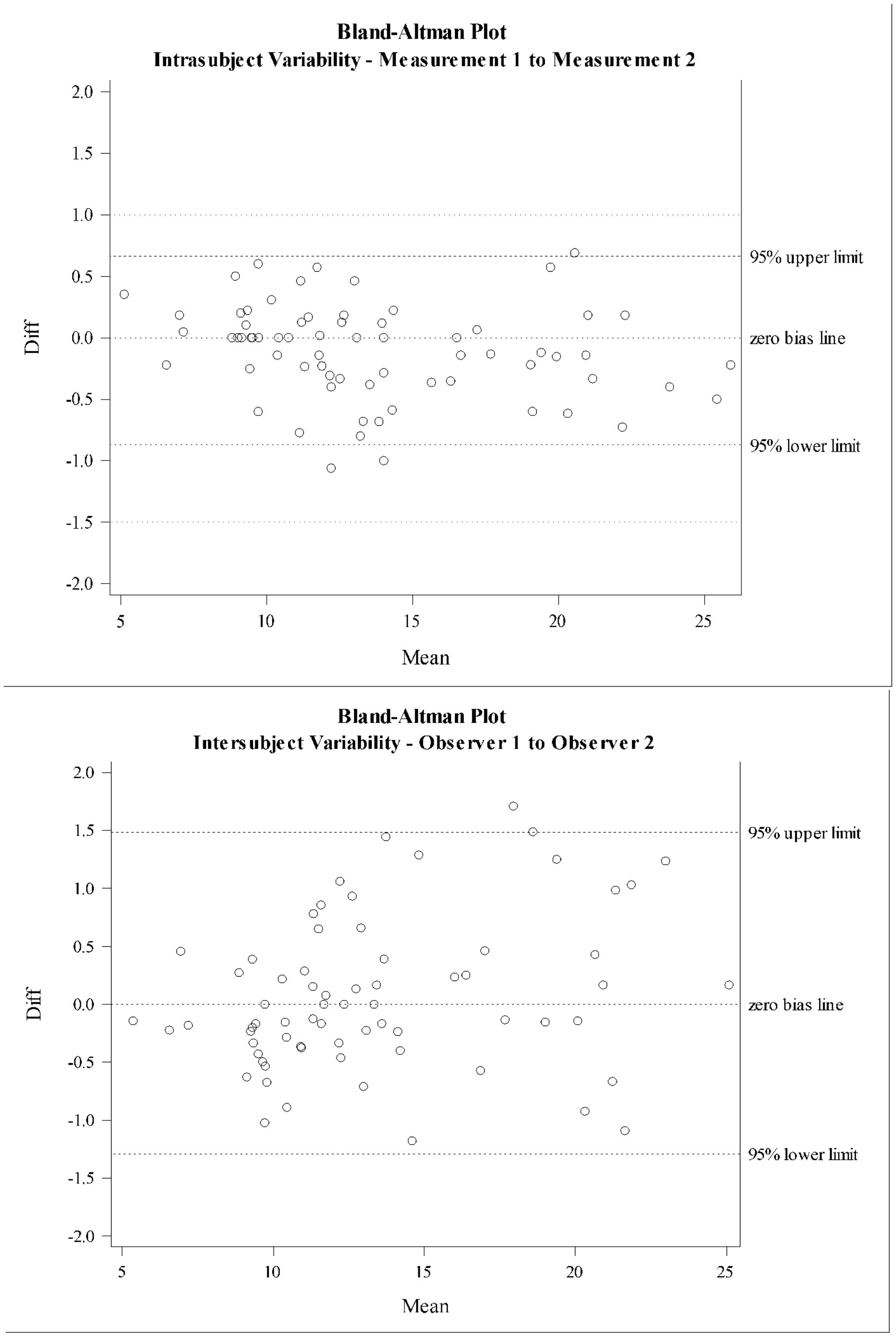
FIG. 6 depicts Land-Altman plots for intraobserver and interobserver variation in E/e' measurement.
Figure 7A:
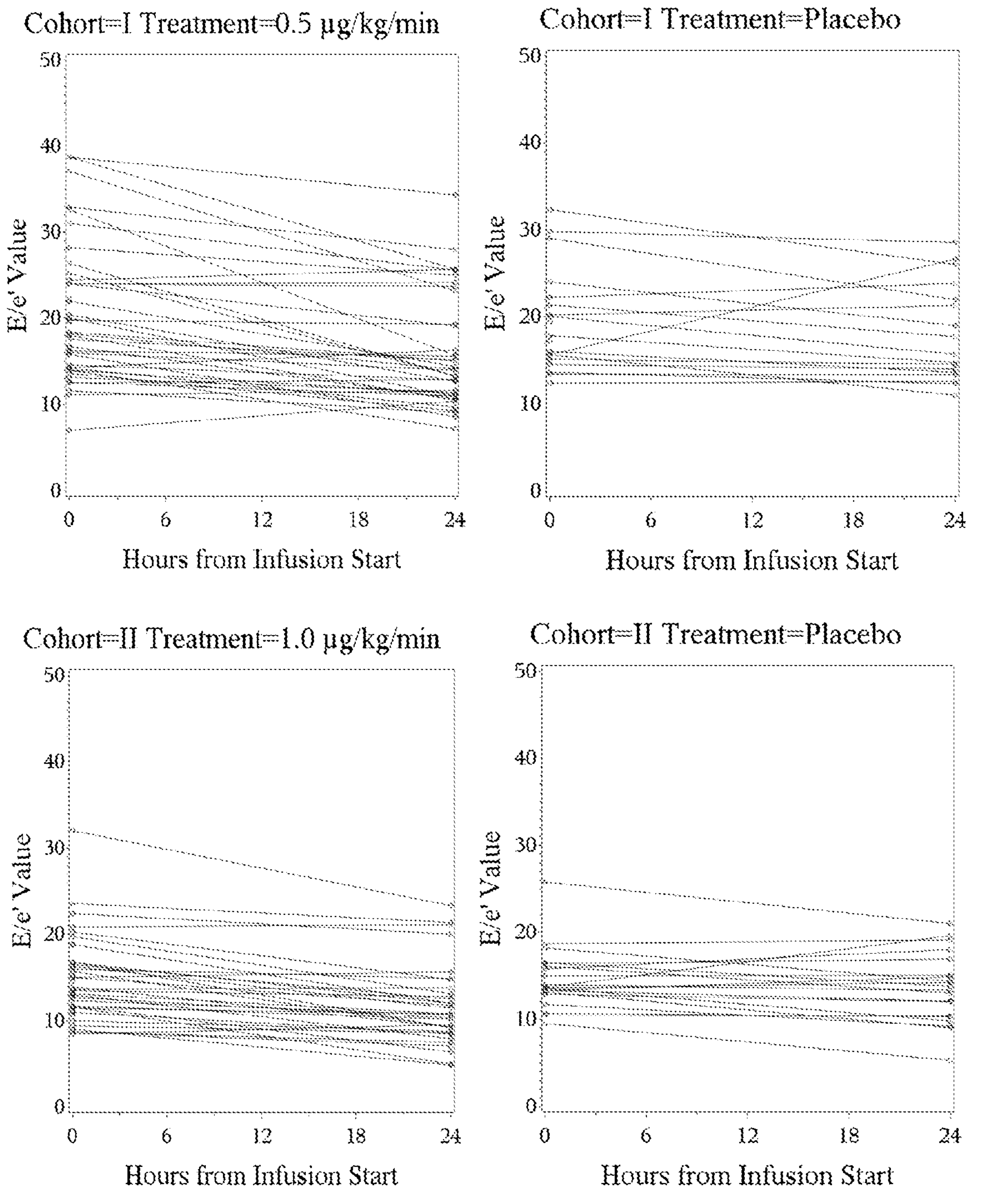
FIG. 7A depicts individual changes from baseline to 24 h in E/e ratio.
Figure 7B:
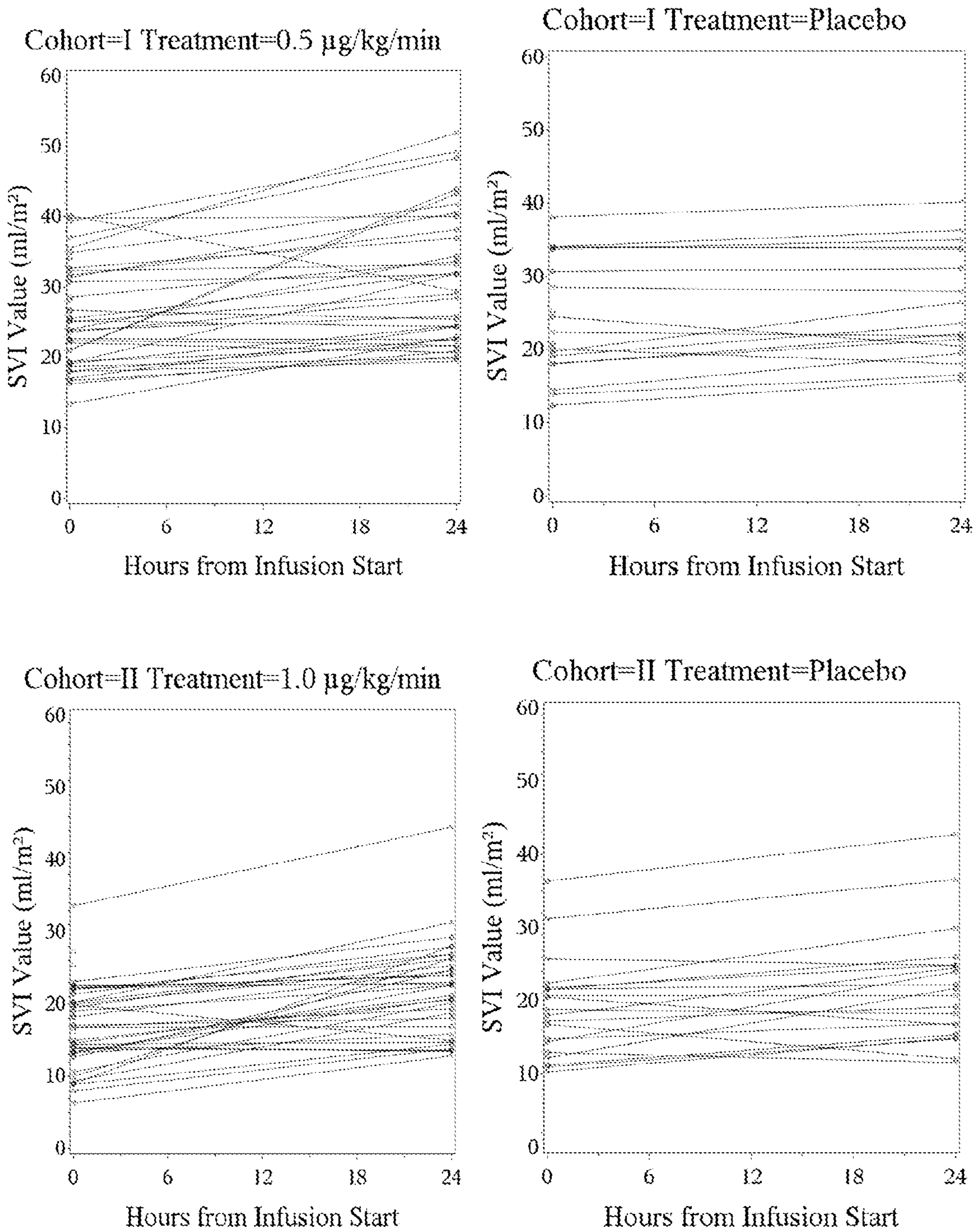
FIG. 7B depicts individual changes from baseline to 24 h in stroke volume index.
Figure 7C:
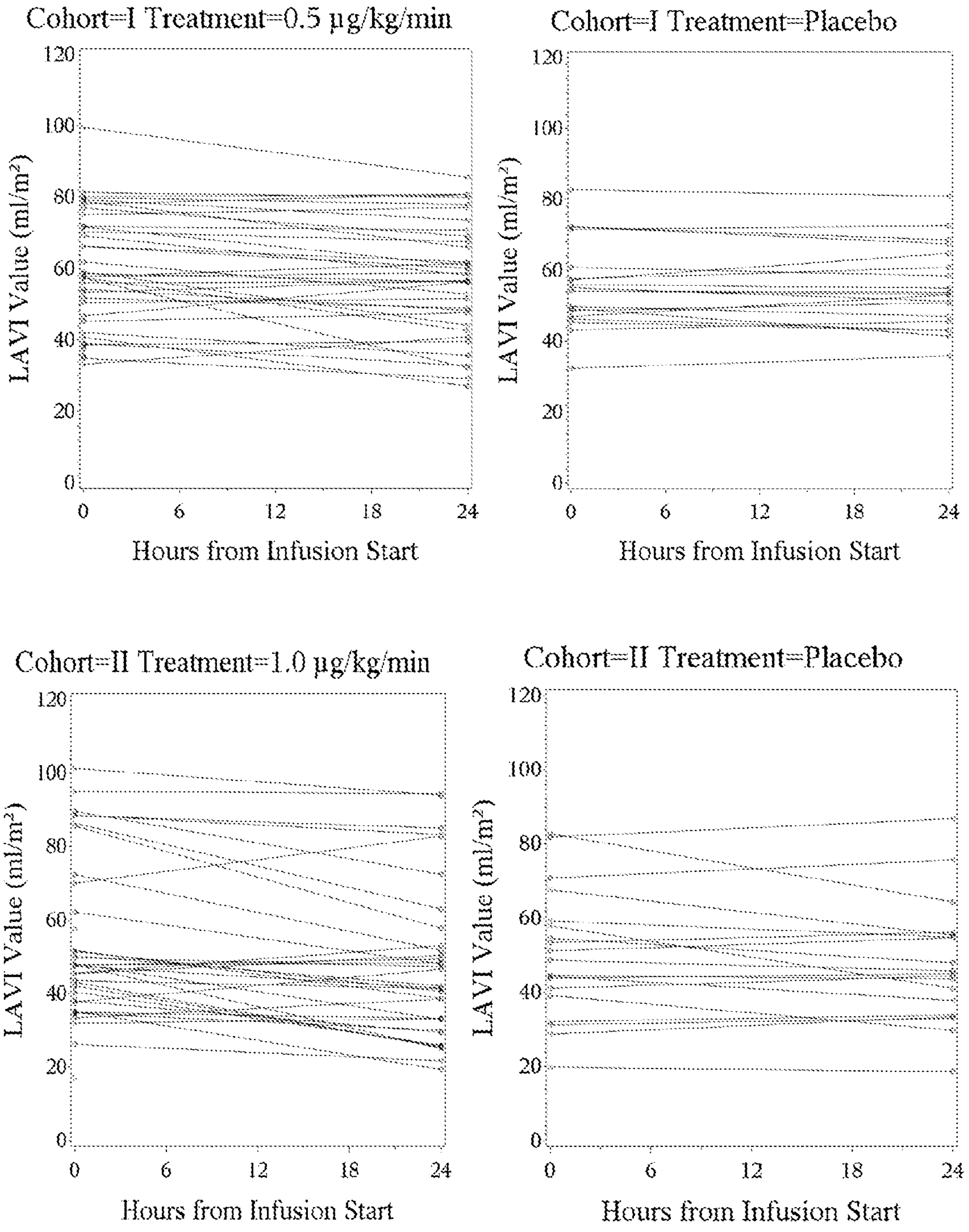
FIG. 7C depicts individual changes from baseline to 24 h in left atrial volume index.
Figure 7D:
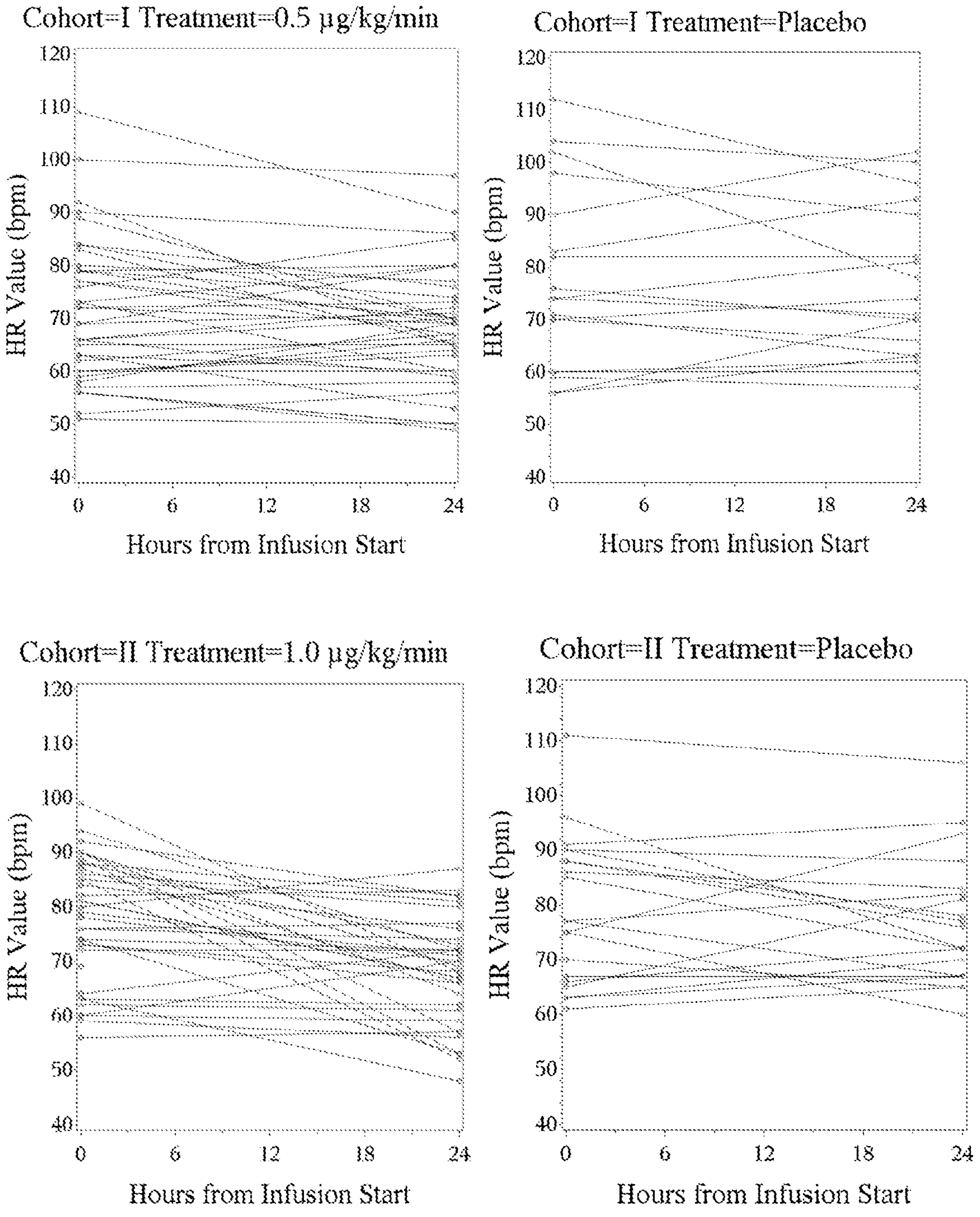
FIG. 7D depicts individual changes from baseline to 24 h in heart rate.
Figure 7E:
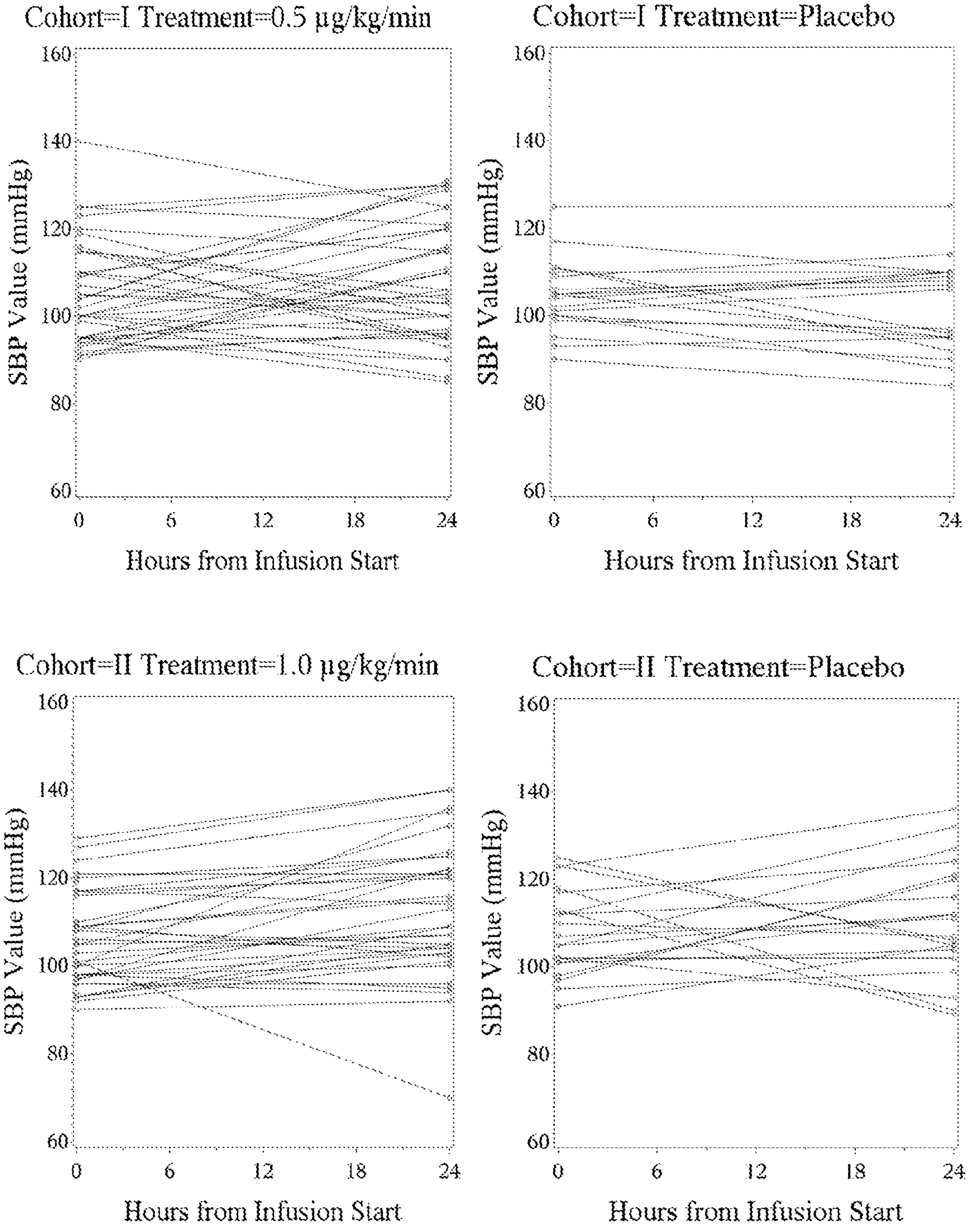
FIG. 7E depicts individual changes from baseline to 24 h in systolic blood pressure.

The study design included a 24 h screening period, a 24 h study drug infusion phase (day 1), a post-treatment phase (days 2-4), and a follow-up visit at day 30 (FIG. 5). Patients could be enrolled at any time after admission. The use of oral medications was permitted during the study with the exception of digoxin. Intravenous diuretics were permitted during the treatment period at stable doses, unless changes were required due to clinically relevant variations of the patient's condition. If treatment with an inotrope was clinically necessary during the infusion period, the investigational product was discontinued. Echocardiography was performed according to international standards at screening, baseline (just before starting study drug infusion), 6, 24 h (just before infusion end), and 48 h after infusion start. Echocardiographic measurements at baseline, 6, 24, and 48 h were evaluated in a blinded fashion by a CoreLab located at the University and Civil Hospital of Brescia, Italy. E/e' ratio was calculated as the ratio between the peak early diastolic mitral flow velocity (E wave) and the mean of the annular lateral (e' lateral) and septal (e' septal) velocities, according to standard guidelines.[20] Intraobserver and interobserver variability in E/e' measurement was tested on the 15% of the recordings and is shown in FIG. 6. Self-reported dyspnoea was assessed using a 100 mm VAS, with zero representing the worst level of dyspnoea and 10 the best breathing condition. Twenty-four hour ECG monitoring was performed using a three-lead device (Mortara industries, Milwaukee, WI, USA) during the day of screening, the infusion period, and the day after (the latter was optional). Analysis was conducted by a blinded CoreLab (ICS Maugeri, Italy). Serial measurements of NT-proBNP throughout the study were analyzed by a central laboratory (Elecsys® proBNP II, Roche®, Basel, Switzerland). Samples for cTnT were taken at baseline, 3, 6, 12, 24, 48, and 72 h and on day 30, and were analyzed by a core laboratory (Elecsys® high-sensitivity assay, Roche®, Basel, Switzerland). AEs were monitored throughout the duration of the study.

Statistical Analysis

The study was designed as a mechanistic and safety study to assess the effects of a 24 h istaroxime infusion in patients hospitalized for AHF. Based on the changes observed in the HORIZON-HF trial, we assumed that a sample size of at least 20 patients in the placebo group in each cohort with 2:1 randomization to istaroxime would provide sufficient power to assess the effect of istaroxime on the main haemodynamic parameters. Analyses were conducted using a pre-specified modified intention-to-treat (mITT) protocol, including all randomized patients in whom study drug infusion had been initiated and with at least none available evaluation of efficacy after the baseline. Biomarker and eGFR values were analyzed using medians and inner/outer quartiles, and active treatment was compared to placebo using the Wilcoxon rank-sum test. Dyspnoea scores by VAS were analyzed using mixed model regression with treatment, center, time point, gender, baseline cTnT, presence of atrial fibrillation, treatment by time point interaction, baseline value, and baseline value by time point interaction in the model. Echocardiographic parameters were compared between treatment groups using linear regression with treatment in the model. Categorical variables were summarized as frequency and percent and compared between treatment groups using the Cochran-Mantel-Haenszel test, controlling for study site. AEs were recorded for all enrolled patients and were summarized as AEs, serious AEs (SAEs), AEs leading to discontinuation, and SAEs leading to death. All analyses were conducted using the SAS® System for Windows™, versions 9.1.3 and 9.4.

Results

Study Population

Patient disposition is summarized in FIG. 1. Enrollment took place at two Italian centers, from October 2013 to March 2015, with the inclusion of 24 patients, and in eight Chinese centers, from November 2016 to July 2018, with the inclusion of 96 patients. Among 144 patients screened, 21 were screening failures and one patient withdrew consent. Additionally, two patients from cohort 2 were excluded from the mITT analysis as pre-specified in the protocol because they withdrew within 2 h before any efficacy assessments were performed due to violation of eligibility criteria. The mITT population included 60 patients in each cohort; 19 on placebo (12 Asian and 7 Caucasian) and 41 on istaroxime 0.5 μg/kg/min in cohort 1 (24 Asian and 17 Caucasian), and 20 on placebo and 40 on istaroxime 1.0 μg/kg/min in cohort 2 (all Asian patients). In the per-protocol analysis, one patient on placebo in cohort 2, two patients on istaroxime 0.5 μg/kg/min, and four patients on istaroxime 1.0 μg/kg/min were excluded due to violations of exclusion criteria (n=2), major Good Clinical Practice violation (Holter was started prior to informed consent form signature), and four patients used prohibited medications (digoxin, dopamine, and levosimendan).

Baseline Haracteristics

Baseline characteristics are shown in Table 1. Besides the higher prevalence of Asian patients in cohort 2 (100% vs. 60% in cohort 1), there were no major differences within each cohort.

TABLE 1

Baseline characteristics

| Variable | Placebo cohort 1 (n = 19) | Istaroxime 0.5 μg/kg/min (n = 41) | Placebo cohort 2 (n = 20) | Istaroxime 1.0 μg/kg/min (n = 40) |
|---|---|---|---|---|
| Age (years) | 57.9 ± 16.5 | 59.7 ± 15.5 | 55.5 ± 16.3 | 52.3 ± 13.0 |
| Male sex | 16 (84.2) | 34 (82.9) | 18 (90.0) | 34 (85.0) |
| Race | | | | |
| Caucasian | 7 (37.0) | 17 (41.5) | — | — |
| Asian | 12 (63.0) | 24 (58.5) | 20 (100) | 40 (100) |
| BMI (kg/m$^2$) | 25.2 ± 3.4 | 25.4 ± 4.0 | 2.37 ± 4.2 | 23.3 ± 3.8 |
| Atrial fibrillation at screening | 5 (26.3) | 8 (19.5) | 6 (30.0) | 11 (27.5) |
| Systolic blood pressure (mmHg) | 104.6 ± 8.3 | 105.0 ± 11.6 | 107.9 ± 9.9 | 106.0 ± 10.4 |
| Heart rate (bpm) | 76.7 ± 17.4 | 71.8 ± 13.3 | 79.2 ± 13.4 | 77.9 ± 11.0 |
| QRS duration (ms) | 135.6 ± 41.6 | 132.9 ± 32.1 | 120.4 ± 22.6 | 126.9 ± 26.5 |
| Dyspnoea VAS score | 69.7 ± 18.3 | 73.6 ± 19.5 | 71.8 ± 24.3 | 71.5 ± 21.0 |
| Ischaemic aetiology | 10 (52.6) | 16 (39.0) | 6 (30.0) | 13 (32.5) |
| Medical history | | | | |
| Diabetes | 5 (26.3) | 14 (34.1) | 4 (20.0) | 6 (15.0) |
| Arterial hypertension | 11 (57.9) | 17 (41.5) | 7 (35.0) | 14 (35.0) |
| Chronic kidney disease | 5 (26.3) | 12 (29.3) | 6 (30.0) | 10 (23.8) |
| Laboratory | | | | |
| Glomerular filtration rate (mL/min/m$^2$) | 85.2 [41.0-95.1] | 74.6 [51.2-88.6] | 73.0 [54.1-96.4] | 78.1 [58.3-91.31 |
| NT-proBNP (pg/mL) | 4215 [2184-6093] | 3437 [1924-6214] | 3830 [1957-9356] | 2818 [1441-5110] |

TABLE 1-continued

| Baseline characteristics | | | | |
|---|---|---|---|---|
| Variable | Placebo cohort 1 (n = 19) | Istaroxime 0.5 μg/kg/min (n = 41) | Placebo cohort 2 (n = 20) | Istaroxime 1.0 μg/kg/min (n = 40) |
| cTnT (ng/mL) | 27.0 [17-42] | 23.0 [16-37] | 19.0 [14-36] | 24.8 [14-38] |
| Medications[a] | | | | |
| ACEi | 10 (52.6) | 25 (61.0) | 13 (65.0) | 27 (67.5) |
| ARB | 6 (31.6) | 11 (26.8) | 5 (25.0) | 6 (15.0) |
| Beta-blockers | 16 (84.2) | 32 (78.1) | 15 (75.0) | 30 (75.0) |
| MRA | 18 (94.7) | 37 (90.2) | 20 (100) | 39 (97.5) |
| Diuretic | 19 (100) | 41 (100) | 20 (100) | 40 (100) |
| Digitalis glycoside[b] | 3 (15.8) | 11 (26.8) | 9 (45.0) | 12 (30.0) |
| Echocardiography | | | | |
| LV end-diastolic volume index ($mL/m^2$) | 127.8 ± 39.9 | 126.1 ± 32.6 | 123.2 ± 49.4 | 118.7 ± 36.2 |
| LV end-systolic volume index ($mL/m^2$) | 97.0 ± 37.1 | 92.2 ± 28.1 | 90.5 ± 40.6 | 85.6 ± 7.2 |
| LV ejection fraction (%) | 25.4 ± 7.3 | 27.4 ± 6.7 | 27.0 ± 7.8 | 28.7 ± 7.2 |
| S' | 3.50 ± 0.78 | 3.66 ± 1.07 | 3.73 ± 1.08 | 3.94 ± 1.09 |
| Stroke volume index ($mL/beat/m^2$) | 24.29 ± 7.93 | 25.88 ± 7.10 | 19.0 6.7 | 17.11 ± 5.69 |
| E/e' ratio | 19.45 ± 5.82 | 20.44 ± 7.87 | 14.62 ± 3.58 | 15.14 ± 5.48 |
| E/A ratio | 2.62 ± 1.17 | 254 ± 1.09 | 2.34 ± 1.13 | 2.08 ± 0.92 |
| Left atrial area ($cm^2$) | 27.8 ± 4.14 | 28.5 ± 5.36 | 24.7 ± 6.03 | 25.9 ± 7.05 |
| Left atrial volume index ($mL/m^2$) | 55.6 ± 12.1 | 58.3 ± 16.6 | 50.1 ± 17.2 | 52.3 ± 21.0 |
| Mitral regurgitation, severe | 9 (47) | 17 (44) | 7 (37) | 19 (49) |
| IVC diameter (mm) | 19.9 ± 3.6 | 21.23 ± 4.6 | 18.7 ± 5.2 | 19.5 ± 5.3 |

Data are shown as mean ± standard deviation, n (%). or median [interquartile range].

ACEi, angiotensin-converting enzyme inhibitor; ARB, angiotensin receptor blocker; BMI. body mass index; cTnT. cardiac troponin T:IVC, inferior vena cava; LV, left ventricular; MRA. mineralocorticoid receptor antagonist; NT-proBNP, N-terminal brain natriuretic peptide; VAS, visual analogue scale.

[a]Medications are those taken prior to the study and may have been maintained through study treatment.

[b]Refers to patients treated before randomization. Digitalis glycosides were not allowed during the study.

All intracohort comparisons are not significant.

Primary Endpoint

The primary endpoint (change in the E/e' ratio from baseline to 24 h) was significantly reduced with both istaroxime doses compared with placebo within each individual cohort. The magnitude of the reduction from baseline was similar with both doses (cohort 1: −4.55±4.75 istaroxime 0.5 g/kg/min vs. −1.55±4.11 placebo, P=0.029; cohort 2: −3.16±2.59 istaroxime 1.0 pg/kg/min vs. −1.08±2.72 placebo, P=0.009) (Table 2, Table 4, and FIG. 2A). In the per-protocol population, results were identical for cohort 1, whereas the E/e' change was −3.19±2.63 in the istaroxime 1.0 g/kg/min group vs. −1.08±2.72 in the placebo cohort 2 group (P=0.009).

TABLE 2

| Echocardiographic parameters change at 24 h | | | | | | |
|---|---|---|---|---|---|---|
| Variable | Placebo cohort 1 (n = 19) | Istaroxime 0.5 μg/kg/min (n = 41) | P-value | Placebo cohort 2 (n = 20) | Istaroxime 1.0 μg/kg/min (n = 40) | P-value |
| LV end-diastolic volume index ($mL/m^2$) | n = 19 | n = 38 | 0.668 | n = 18 | n = 33 | 0.414 |
| | 0.53 ± 6.94 | −0.20 ± 5.45 | | −4.34 ± 9.88 | −2.08 ± 9.05 | |
| LV end-systolic volume index ($mL/m^2$) | n = 19 | n = 38 | 0.118 | n = 18 | n = 33 | 0.914 |
| | −0.97 ± 5.26 | −3.78 ± 6.76 | | −6.53 ± 9.83 | −6.23 ± 9.23 | |
| LV ejection fraction (%) | n = 19 | n = 38 | 0.089 | n = 18 | n = 33 | 0.423 |
| | 1.26 ± 2.54 | 3.03 ± 4.04 | | 2.83 ± 4.20 | 3.82 ± 4.14 | |
| Stroke volume index ($mL/beat/m^2$) | n = 17 | n = 34 | 0.034 | n = 19 | n = 34 | 0.090 |
| | 1.65 ± 2.76 | 5.33 ± 6.67 | | 3.18 ± 4.02 | 5.49 ± 4.98 | |
| E/e' | n = 17 | n = 37 | 0.029 | n = 19 | n = 33 | 0.009 |
| | −1.55 ± 4.11 | −4.55 ± 4.75 | | −1.08 ± 2.72 | −3.16 ± 2.59 | |
| E/A ratio | n = 9 | n = 16 | 0.042 | n = 12 | n = 22 | 0.029 |
| | 0.13 ± 0.98 | −0.64 ± 0.79 | | 0.18 ± 0.80 | −0.65 ± 1.10 | |
| Left atrial area ($cm^2$) | n = 19 | n = 35 | 0.032 | n = 18 | n = 33 | 0.024 |
| | −0.36 ± 1.33 | −1.70 ± 2.46 | | −0.22 ± 2.32 | −2.21 ± 3.18 | |

TABLE 2-continued

| Echocardiographic parameters change at 24 h | | | | | | |
|---|---|---|---|---|---|---|
| Variable | Placebo cohort 1 (n = 19) | Istaroxime 0.5 µg/kg/min (n = 41) | P-value | Placebo cohort 2 (n = 20) | Istaroxime 1.0 µg/kg/min (n = 40) | P-value |
| Left atrial volume index (mL/m²) | n = 19 | n = 35 | 0.037 | n = 18 | n = 33 | 0.091 |
| | 0.46 ± 3.86 | −4.32 ± 7.28 | | −2.65 + 7.46 | −7.32 ± 10.0 | |
| S' (cm/s) | n = 18 | n = 39 | 0.029 | n = 19 | n = 34 | 0.039 |
| | 0.11 ± 0.85 | 0.68 ± 0.91 | | 0.16 ± 1.18 | 0.81 ± 1.01 | |

Data are shown as mean ± standard deviation.
LV, left ventricular

Secondary Endpoints

Figure 2:
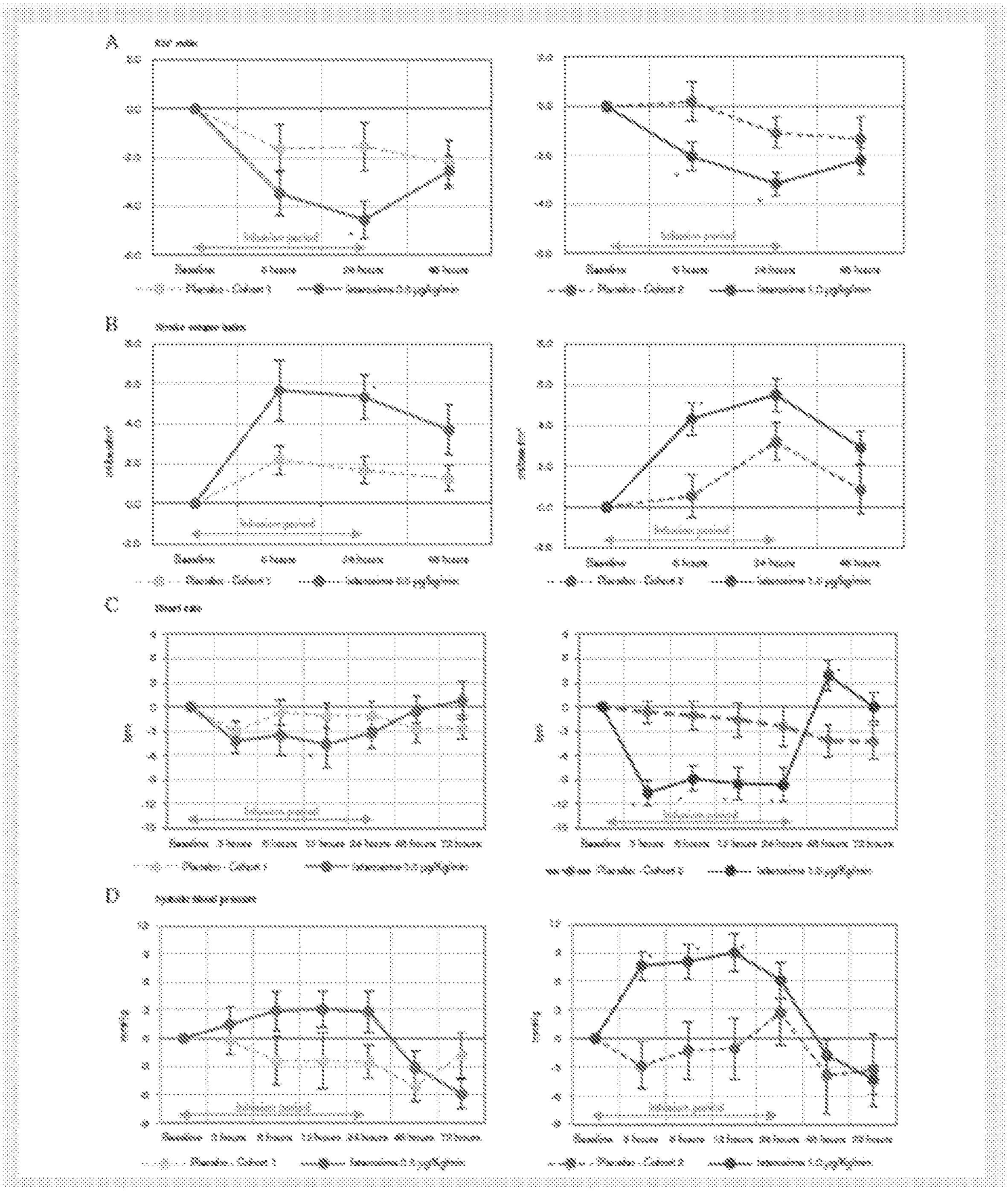
FIG. 2 depicts changes in echocardiographic and haemodynamic parameters: (A) E/e' ratio, (B) stroke volume index, (C) heart rate, (D) systolic blood pressure (Data are shown as mean change from baseline. *P<0.05).

Both istaroxime doses increased stroke volume index from baseline to 24 h (Table 2, Table 4, and FIG. 2B). Changes in LVEF and left ventricular volumes did not reach statistical significance compared to placebo. Treatment with istaroxime was associated with improvement of other echocardiographic parameters such as E/A ratio, left atrial dimensions and inferior vena cava diameter (Table 2 and Table 4). HR decreased from baseline by about 3 bpm with istaroxime 0.5 µg/kg/min and by 8-9 bpm with istaroxime 1.0 µg/kg/min with significant changes vs. placebo at 3 to 24 h in the high-dose group. SBP increased from baseline by about 3 mmHg with istaroxime 0.5 µg/kg/min and by 6-8 mmHg with istaroxime 1.0 µg/kg/min reaching statistical significance compared to placebo at 3 to 12 h in istaroxime 1.0 µg/kg/min group (FIG. 2C, 2D and Table 4). Individual changes from baseline to 24 h in the main echocardiographic parameters and vital signs are reported in FIG. 7. None of the other secondary endpoints showed significant differences between istaroxime and placebo (Table 5). Overall diuresis during the 24 h infusion was numerically higher in patients treated with istaroxime compared to placebo (Table 3).

TABLE 3

| Diuresis over 24h during and after study drug infusion | | | | |
|---|---|---|---|---|
| | Placebo cohort 1 (n = 19) | Istaroxime 0.5 µg/kg/min (n = 41) | Placebo cohort 2 (n = 20) | Istaroxime 1.0 µg/kg/min (n = 40) |
| 0-24 h (mL) | n = 14<br>1850<br>[1050-2530] | n = 30<br>2700<br>[2000-3000] | n = 20<br>1515<br>[1130-1965] | n = 38<br>1975<br>[1530-2750] |
| 24-48 h (mL) | n = 14<br>2300<br>[1100-2850] | n = 29<br>1800<br>[1200-2300] | n = 19<br>1820<br>[1200-2000] | n = 33<br>1260<br>[1010-1450] |
| 48-72 h (mL) | n = 13<br>2000<br>[1500-2600] | n = 30<br>1650<br>[1000-2000] | n = 19<br>1810<br>[1230-2290] | n = 33<br>1350<br>[1000-1750] |

Data are shown as median [interquartile range].

TABLE 4

| Hemodynamic and echocardiographic parameters at baseline and changes during and after study drug infusion | | | | | | |
|---|---|---|---|---|---|---|
| Variable | Placebo cohort 1 (n = 19) | Istaroxime 0.5 µg/Kg/min (n = 41) | p-value Cohort 1 | Placebo cohort 2 (n = 20) | Istaroxime 1.0 µg/Kg/min (n = 40) | p-value Cohort 2 |
| SBP (mmHg) | | | | | | |
| Baseline | 104.63 ± 8.29 | 104.95 ± 11.60 | 0.829 | 107.85 ± 9.86 | 106.00 ± 10.39 | 0.548 |
| 3 hours | −0.26 ± 6.43 | 1.49 ± 11.15 | 0.446 | −2.85 ± 10.96 | 7.63 ± 9.22 | <0.001 |
| 6 hours | −2.37 ± 11.05 | 2.92 ± 13.38 | 0.071 | −1.25 ± 13.52 | 8.08 ± 11.06 | 0.011 |
| 12 hours | −2.37 ± 13.11 | 3.13 ± 11.95 | 0.070 | −1.05 ± 13.75 | 9.00 ± 11.75 | 0.006 |
| 24 hours | −2.47 ± 7.56 | 2.82 ± 14.21 | 0.069 | 2.70 ± 15.52 | 6.11 ± 11.17 | 0.542 |
| 48 hours | −5.11 ± 6.98 | −3.10 ± 11.41 | 0.381 | −3.84 ± 17.31 | −1.73 ± 9.50 | 0.692 |
| HR (bpm) | | | | | | |
| Baseline | 76.68 ± 17.44 | 71.83 ± 13.33 | 0.502 | 79.20 ± 13.40 | 77.88 ± 10.95 | 0.631 |
| 3 hours | −3.05 ± 9.18 | −4.21 ± 8.80 | 0.124 | −0.65 ± 5.97 | −10.61 ± 10.04 | <0.001 |
| 6 hours | −0.68 ± 12.27 | −3.51 ± 9.91 | 0.074 | −1.05 ± 7.80 | −8.89 ± 9.83 | 0.001 |
| 12 hours | −1.05 ± 10.55 | −4.59 ± 9.01 | 0.014 | −1.58 ± 9.05 | −9.49 ± 11.96 | 0.005 |
| 24 hours | −1.00 ± 9.37 | −3.26 ± 8.79 | 0.071 | −2.40 ± 10.68 | −9.61 ± 12.10 | 0.004 |
| 48 hours | −2.74 ± 11.61 | −0.37 ± 10.09 | 0.774 | −4.16 ± 8.58 | 3.86 ± 11.94 | 0.011 |
| EDV (ml) | | | | | | |
| Baseline | 231.3 ± 76.2 | 232.0 ± 71.3 | 0.973 | 217.6 ± 84.0 | 211.6 ± 72.5 | 0.783 |
| 6 hours | 0.63 ± 10.37 | 1.47 ± 13.88 | 0.816 | −7.95 ± 19.05 | 1.35 ± 16.67 | 0.070 |
| 24 hours | 0.95 ± 12.20 | −0.71 ± 10.16 | 0.589 | −7.61 ± 17.16 | −3.67 ± 16.44 | 0.424 |
| 48 hours | 1.47 ± 10.71 | −0.59 ± 14.43 | 0.584 | −9.72 ± 17.90 | −3.18 ± 15.09 | 0.172 |
| EDV Index (ml/m²) | | | | | | |
| Baseline | 127.8 ± 39.9 | 126.1 ± 32.6 | 0.860 | 123.2 ± 49.4 | 118.7 ± 36.2 | 0.693 |
| 6 hours | 0.26 ± 5.82 | 0.85 ± 8.06 | 0.779 | −4.50 ± 10.8 | 0.64 ± 9.36 | 0.075 |
| 24 hours | 0.53 ± 6.94 | −0.20 ± 5.45 | 0.668 | −4.34 ± 9.88 | −2.08 ± 9.05 | 0.414 |
| 48 hours | 0.78 ± 6.10 | −0.07 ± 7.96 | 0.684 | −5.54 ± 10.0 | −1.86 ± 8.52 | 0.174 |

TABLE 4-continued

Hemodynamic and echocardiographic parameters at baseline and changes during and after study drug infusion

| Variable | Placebo cohort 1 (n = 19) | Istaroxime 0.5 μg/Kg/min (n = 41) | p-value Cohort 1 | Placebo cohort 2 (n = 20) | Istaroxime 1.0 μg/Kg/min (n = 40) | p-value Cohort 2 |
|---|---|---|---|---|---|---|
| ESV (ml) | | | | | | |
| Baseline | 175.7 ± 70.6 | 169.9 ± 61.4 | 0.750 | 160.1 ± 69.3 | 153.4 ± 64.3 | 0.722 |
| 6 hours | −1.95 ± 9.81 | −4.89 ± 13.12 | 0.391 | −7.95 ± 17.03 | −4.62 ± 16.80 | 0.494 |
| 24 hours | −1.74 ± 9.70 | −7.11 ± 12.66 | 0.110 | −11.83 ± 17.55 | −11.39 ± 17.13 | 0.931 |
| 48 hours | 1.42 ± 11.33 | −2.57 ± 13.05 | 0.747 | −6.13 ± 14.929 | −8.09 ± 19.78 | 0.540 |
| ESV Index ($ml/m^2$) | | | | | | |
| Baseline | 97.0 ± 37.1 | 92.2 ± 28.1 | 0.587 | 90.5 ± 40.6 | 85.6 ± 32.1 | 0.618 |
| 6 hours | −1.13 ± 5.52 | −2.54 ± 7.20 | 0.457 | −4.45 ± 9.77 | −2.42 ± 9.22 | 0.453 |
| 24 hours | −0.97 ± 5.26 | −3.78 ± 6.76 | 0.118 | −6.53 ± 9.83 | −6.23 ± 9.23 | 0.914 |
| 48 hours | −0.84 ± 6.33 | −1.19 ± 7.65 | 0.864 | −6.40 ± 8.61 | −4.46 ± 10.6 | 0.510 |
| LVEF (%) | | | | | | |
| Baseline | 25.4 ± 7.3 | 27.4 ± 6.7 | 0.305 | 27.0 ± 7.8 | 28.7 ± 7.2 | 0.407 |
| 6 hours | 1.32 ± 3.07 | 2.03 ± 3.4 | 0.446 | 0.95 ± 2.82 | 2.35 ± 4.28 | 0.206 |
| 24 hours | 1.26 ± 2.54 | 3.03 ± 4.04 | 0.089 | 2.83 ± 4.20 | 3.82 ± 4.14 | 0.423 |
| 48 hours | 0.68 ± 2.96 | 1.19 ± 3.68 | 0.607 | 1.83 ± 4.06 | 2.06 ± 4.97 | 0.869 |
| SVI ($ml/beat/m^2$) | | | | | | |
| Baseline | 24.29 ± 7.93 | 25.88 ± 7.10 | 0.444 | 19.0 ± 6.7 | 17.11 ± 5.69 | 0.267 |
| 6 hours | 2.19 ± 3.00 | 5.66 ± 8.88 | 0.114 | 0.54 ± 4.79 | 4.32 ± 4.63 | 0.006 |
| 24 hours | 1.65 ± 2.76 | 5.33 ± 6.67 | 0.034 | 3.18 ± 4.02 | 5.49 ± 4.98 | 0.090 |
| 48 hours | 1.24 ± 2.64 | 3.68 ± 7.39 | 0.184 | 0.85 ± 5.07 | 2.91 ± 4.57 | 0.137 |
| CI ($l/min/m^2$) | | | | | | |
| Baseline | 1.80 ± 0.50 | 1.89 ± 0.52 | 0.496 | 1.55 ± 0.53 | 1.36 ± 0.46 | 0.150 |
| 6 hours | 0.15 ± 0.32 | 0.20 ± 0.45 | 0.672 | −0.05 ± 0.45 | 0.15 ± 0.44 | 0.103 |
| 24 hours | 0.17 ± 0.36 | 0.27 ± 0.37 | 0.370 | 0.09 ± 0.39 | 0.15 ± 0.44 | 0.613 |
| 48 hours | 0.07 ± 0.26 | 0.19 ± 0.43 | 0.284 | −0.08 ± 0.47 | 0.20 ± 0.41 | 0.025 |
| E wave (cm/s) | | | | | | |
| Baseline | 102.0 ± 18.1 | 97.3 ± 30.6 | 0.540 | 85.4 ± 23.6 | 89.2 ± 24.6 | 0.565 |
| 6 hours | −3.16 ± 11.47 | −4.35 ± 14.39 | 0.755 | 0.85 ± 10.43 | −10.19 ± 17.82 | 0.014 |
| 24 hours | −3.29 ± 13.81 | −8.14 ± 17.64 | 0.323 | −5.84 ± 11.09 | −14.06 ± 24.07 | 0.167 |
| 48 hours | −7.74 ± 12.27 | −5.21 ± 17.90 | 0.583 | −3.32 ± 13.36 | −11.53 ± 20.15 | 0.118 |
| A wave (cm/s) | | | | | | |
| Baseline | 46.7 ± 21.9 | 42.8 ± 17.1 | 0.613 | 41.1 ± 17.3 | 45.9 ± 19.4 | 0.449 |
| 6 hours | 1.10 ± 10.52 | 1.76 ± 13.57 | 0.895 | 1.92 ± 10.69 | 5.88 ± 17.39 | 0.476 |
| 24 hours | −0.78 ± 6.67 | 5.13 ± 10.99 | 0.158 | −1.75 ± 8.68 | 9.00 ± 18.86 | 0.072 |
| 48 hours | 0.40 ± 8.38 | −0.94 ± 12.22 | 0.764 | 2.33 ± 13.27 | 5.30 ± 13.04 | 0.578 |
| E/A ratio | | | | | | |
| Baseline | 2.62 ± 1.17 | 2.54 ± 1.09 | 0.861 | 2.34 ± 1.13 | 2.08 ± 0.92 | 0.440 |
| 6 hours | −0.21 ± 0.92 | −0.28 ± 0.87 | 0.839 | −0.06 ± 0.85 | −0.35 ± 0.93 | 0.360 |
| 24 hours | 0.13 ± 0.98 | −0.64 ± 0.79 | 0.042 | 0.18 ± 0.80 | −0.65 ± 1.10 | 0.029 |
| 48 hours | −0.11 ± 0.70 | −0.28 ± 1.04 | 0.662 | −0.28 ± 0.83 | −0.36 ± 0.98 | 0.828 |
| e' (cm/s) | | | | | | |
| Baseline | 5.50 ± 1.25 | 5.20 ± 1.89 | 0.524 | 5.93 ± 1.48 | 6.30 ± 1.93 | 0.449 |
| 6 hours | 0.34 ± 0.94 | 0.63 ± 1.02 | 0.305 | 0.16 ± 1.37 | −0.03 ± 1.13 | 0.594 |
| 24 hours | 0.28 ± 0.88 | 0.94 ± 1.09 | 0.029 | 0.18 ± 1.51 | 0.10 ± 1.77 | 0.867 |
| 48 hours | 0.16 ± 1.31 | 0.32 ± 0.73 | 0.541 | 0.47 ± 1.70 | 0.19 ± 1.83 | 0.574 |
| E/e' ratio | | | | | | |
| Baseline | 19.45 ± 5.82 | 20.44 ± 7.87 | 0.628 | 14.62 ± 3.58 | 15.14 ± 5.48 | 0.705 |
| 6 hours | −1.66 ± 4.31 | −3.48 ± 5.47 | 0.213 | 0.19 ± 3.53 | −2.05 ± 3.69 | 0.034 |
| 24 hours | −1.55 ± 4.11 | −4.55 ± 4.75 | 0.029 | −1.08 ± 2.72 | −3.16 ± 2.59 | 0.009 |
| 48 hours | −2.27 ± 4.31 | −2.56 ± 3.67 | 0.792 | −1.32 ± 3.77 | −2.21 ± 3.19 | 0.367 |
| LAA ($cm^2$) | | | | | | |
| Baseline | 27.77 ± 4.14 | 28.53 ± 5.36 | 0.593 | 24.74 ± 6.03 | 25.92 ± 7.05 | 0.534 |
| 6 hours | −0.09 ± 1.44 | −0.38 ± 1.92 | 0.567 | −0.95 ± 2.09 | −1.03 ± 2.33 | 0.900 |
| 24 hours | −0.36 ± 1.33 | −1.70 ± 2.46 | 0.032 | −0.22 ± 2.32 | −2.21 ± 3.18 | 0.024 |
| 48 hours | −0.48 ± 0.85 | −2.01 ± 2.81 | 0.024 | −0.61 ± 2.70 | −0.94 ± 2.90 | 0.695 |
| LAV (ml) | | | | | | |
| Baseline | 100.3 ± 22.7 | 106.2 ± 29.3 | 0.448 | 88.8 ± 29.7 | 92.3± 37.3 | 0.725 |
| 6 hours | −1.06 ± 11.5 | 0.05 ± 8.59 | 0.715 | −6.53 ± 10.5 | −4.94 ± 14.2 | 0.673 |

TABLE 4-continued

Hemodynamic and echocardiographic parameters at baseline and changes during and after study drug infusion

| Variable | Placebo cohort 1 (n = 19) | Istaroxime 0.5 μg/Kg/min (n = 41) | p-value Cohort 1 | Placebo cohort 2 (n = 20) | Istaroxime 1.0 μg/Kg/min (n = 40) | p-value Cohort 2 |
|---|---|---|---|---|---|---|
| 24 hours | −0.89 ± 7.00 | −7.94 ± 13.2 | 0.036 | −5.00 ± 13.5 | −12.94 ± 17.6 | 0.104 |
| 48 hours | −0.95 ± 5.65 | −9.17 ± 15.8 | 0.034 | −6.61 ± 13.5 | −6.67 ± 17.3 | 0.991 |
| LAVI (mL/m$^2$) | | | | | | |
| Baseline | 55.6 ± 12.1 | 58.3 ± 16.6 | 0.521 | 50.1 ± 17.2 | 52.3 ± 21.0 | 0.691 |
| 6 hours | −0.04 ± 4.74 | −0.51 ± 6.64 | 0.673 | −3.75 ± 5.94 | −2.86 ± 7.97 | 0.673 |
| 24 hours | −0.46 ± 3.86 | −4.32 ± 7.28 | 0.037 | −2.65 ± 7.46 | −7.32 ± 10.0 | 0.091 |
| 48 hours | −0.57 ± 3.08 | −5.01 ± 8.96 | 0.042 | −3.57 ± 7.61 | −3.80 ± 10.3 | 0.933 |
| S' (cm/s) | | | | | | |
| Baseline | 3.50 ± 0.78 | 3.66 ± 1.07 | 0.566 | 3.73 ± 1.08 | 3.94 ± 1.09 | 0.478 |
| 6 hours | 0.34 ± 0.80 | 0.63 ± 1.06 | 0.298 | 0.05 ± 1.03 | 1.00 ± 0.95 | 0.001 |
| 24 hours | 0.11 ± 0.85 | 0.68 ± 0.91 | 0.029 | 0.16 ± 1.18 | 0.81 ± 1.01 | 0.039 |
| 48 hours | 0.32 ± 0.79 | 0.22 ± 0.81 | 0.685 | −0.05 ± 0.98 | 0.26 ± 0.77 | 0.207 |
| TAPSE (mm) | | | | | | |
| Baseline | 15.1 ± 3.0 | 17.3 ± 4.3 | 0.053 | 14.6 ± 3.8 | 14.3 ± 4.0 | 0.796 |
| 6 hours | 0.47 ± 1.55 | 0.41 ± 2.35 | 0.926 | 0.29 ± 2.57 | 1.56 ± 3.13 | 0.156 |
| 24 hours | 1.47 ± 2.24 | 0.73 ± 2.15 | 0.260 | 0.82 ± 2.30 | 1.16 ± 3.73 | 0.740 |
| 48 hours | 0.50 ± 1.86 | −0.34 ± 2.47 | 0.209 | 1.06 ± 2.64 | 0.31 ± 2.69 | 0.365 |
| PASP (mmHg) | | | | | | |
| Baseline | 51.06 ± 12.72 | 54.15 ± 13.03 | 0.416 | 46.07 ± 12.85 | 42.58 ± 13.94 | 0.415 |
| 6 hours | −3.76 ± 6.67 | −4.21 ± 5.77 | 0.812 | −3.47 ± 6.75 | −2.60 ± 9.13 | 0.752 |
| 24 hours | −6.50 ± 9.15 | −10.89 ± 8.98 | 0.170 | −4.92 ± 8.85 | −4.76 ± 13.17 | 0.969 |
| 48 hours | −8.53 ± 8.77 | −11.18 ± 9.58 | 0.380 | −6.43 ± 10.01 | −3.00 ± 7.66 | 0.233 |
| IVC diameter (mm) | | | | | | |
| Baseline | 19.89 ± 3.57 | 21.15 ± 4.64 | 0.303 | 18.67 ± 5.17 | 19.53 ± 5.33 | 0.574 |
| 6 hours | −0.43 ± 3.39 | −2.41 ± 2.69 | 0.020 | 0.29 ± 2.28 | −1.24 ± 4.86 | 0.071 |
| 24 hours | −1.06 ± 2.65 | −4.30 ± 3.48 | 0.001 | −0.06 ± 2.70 | −2.23 ± 4.13 | 0.097 |
| 48 hours | −2.12 ± 2.80 | −4.16 ± 3.26 | 0.030 | −0.71 ± 2.93 | −2.19 ± 4.13 | 0.196 |

All data are shown in TABLE 4 as mean ± standard deviation with the exception of mitral regurgitation: number (%) patients severe at baseline, median change in scoring from baseline. Legend: CI Cardiac index; EDV Left ventricle end diastolic volume; ESV Left ventricle end systolic volume; HR heart rate; IVC inferior vena cava; LAA left atrium area; LA VI left atrium volume index; L VEF Left ventricle ejection fraction; PASP pulmonary artery systolic pressure; SBP systolic blood pressure; SVI Stroke volume index; TAPSE Tricuspid annular plane systolic excursion.

TABLE 5

Secondary endpoints

| Endpoint | Placebo cohort 1 (n = 19) | Istaroxime 0.5 μg/Kg/min (n = 41) | Placebo cohort 2 (n = 20) | Istaroxime 1.0 μg/Kg/min (n = 40) |
|---|---|---|---|---|
| Dyspnoea VAS score | | | | |
| 3 hours | 1.332 (−2.259-4.922) | 4.113 (0.810-7.417) | 4.195 (0.249-8.148) | 4.212 (0.916-7.507) |
| 6 hours | 2.653 (−1.724-7.030) | 6.582 (2.844-10.319) | 3.150 (−1.889-8.188) | 8.637 (4.662-12.611) |
| 12 hours | 5.792 (0.994-10.591) | 6.772 (2.791-10.753) | 6.336 (0.476-12.196) | 9.076 (4.515-13.636) |
| 24 hours | 11.274 (5.964-16.585) | 9.276 (4.992-13.559) | 8.578 (2.341-14.815) | 13.332 (8.472-18.193) |
| 48 hours | 12.170 (6.445-17.896) | 10.948 (6.419-15.477) | 8.434 (1.547-15.330) | 10.075 (4.830-15.320) |
| NT-proBNP (pg/mL) | | | | |
| 24 hours | −611 (−1220, −97) | 120 (−369, 1089) | −859 (−2073, −209) | −214 (−893, 373) |
| 48 hours | −1089 (−2222, −238) | −431 (−1232, 24) | −1089 (−3217, −300) | −563 (−1542, −27) |
| 72 hours | −649 (−2190, 129) | −802 (−1441, −338) | −2298 (−3925, −469) | −528 (−2097, 89) |
| Worsening heart failure to day 4 (%) | 1 (5.3%) | 1 (2.4%) | 1 (5.3%) | 3 (7.5%) |

TABLE 5-continued

| Secondary endpoints | | | | |
|---|---|---|---|---|
| Endpoint | Placebo cohort 1 (n = 19) | Istaroxime 0.5 μg/Kg/min (n = 41) | Placebo cohort 2 (n = 20) | Istaroxime 1.0 μg/Kg/min (n = 40) |
| Hospital readmission/ ED visits (%) to Day 30 | 1 (5.3%) | 4 (9.8%) | 1 (5.0%) | 4 (10%) |
| Length of stay (Days) | 8.0 (6.0-11.0) | 7.0 (5.0-9.0) | 7.0 (5.0-10.5) | 7.0 (5.0-11.0) |

Changes from baseline during and after study drug infusion (Dyspnoea VAS score and NT-proBNP are shown as changes from baseline value; Dyspnoea VAS score is expressed as the mean (95% CI). NT-proBNP and length of stay is expressed as the median (IQR).

Other variables are expressed as count (%);

Legend: ED emergency department, NT-proBNP N-terminal pro brain natriuretic peptide; VAS visual analog scale).

Safety Endpoints

Figure 3:
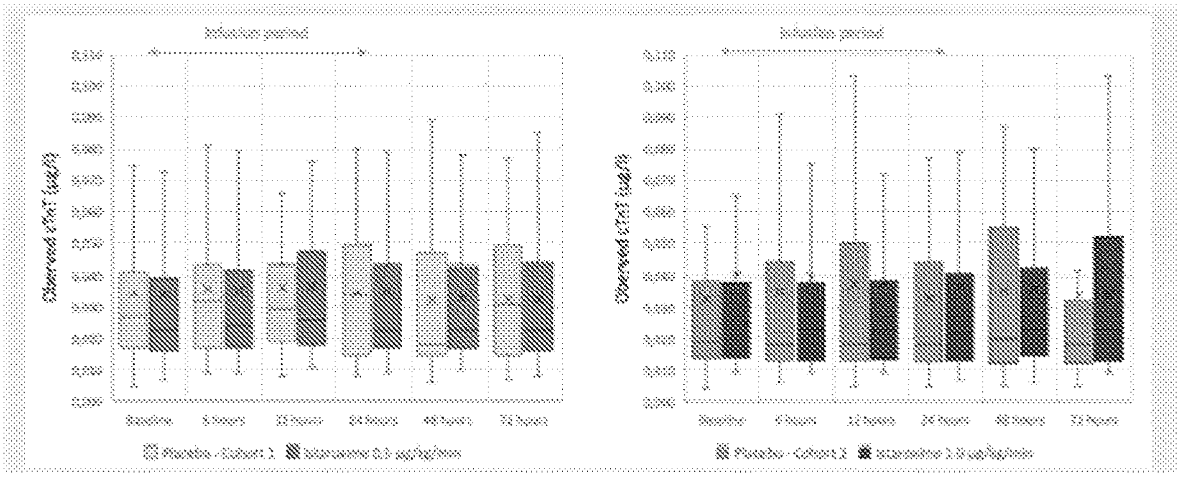
FIG. 3 depicts box and whisker plot for cardiac troponin T (cTnT).

No significant changes in cardiac troponin absolute values were observed during and after istaroxime infusion (FIG. 3 and Tables 6 and 7). Renal function measured by eGFR generally increased with both istaroxime doses over 24 h in contrast to placebo where a decrease was observed (Table 6). No other clinically meaningful changes in laboratory parameters were observed comparing istaroxime vs. placebo. In particular, worsening of hepatic function or signs of hepatic drug toxicity were not reported during the study (data not shown). Data from 24 h Holter monitoring showed no differences in clinically significant arrhythmias between istaroxime and placebo groups (Table 8). The summary of AEs is reported in Table 9. The rate of SAEs did not show meaningful differences in the three arms. One patient died in the istaroxime 1.0 μg/kg/min group within the 30-day study period (cardiogenic shock); one additional cardiac death was recorded after day 30. Analysis of treatment emergent adverse drug reactions showed that the number of patients experiencing cardiovascular AEs was numerically higher in the placebo group. There was a substantially higher rate of patients experiencing gastrointestinal events (mainly abdominal pain, nausea, and vomiting) in the istaroxime 1.0 μg/kg/min group (study drug was discontinued in one patient due to nausea and in one patient due to vomiting concomitant to renal artery embolism). The rate of injection site reactions was high in all patients treated with istaroxime and short intravenous catheters, requiring the change of peripheral line and/or use of peripheral long line or a central line (study drug was discontinued only in one patient treated with istaroxime 1.0 μg/kg/min).

TABLE 6

| Changes in cardiac TnT and eGFR during and after study drug infusion. | | | | |
|---|---|---|---|---|
| Endpoint | Placebo cohort 1 (n = 19) | Istaroxime 0.5 μg/Kg/min (n = 41) | Placebo cohort 2 (n = 20) | Istaroxime 1.0 μg/Kg/min (n = 40) |
| cTnT | | | | |
| 3 hours | 0 (−1.5, 2.0) | 0 (−2.5, 1.4) | 0 (−0.8, 0.5) | −0.5 (−2.0, 0.5) |
| 6 hours | 0 (−2.8, 5.5) | 0 (−1.5, 2.5) | 0.3 (−0.5, 2.5) | 0.5 (−1.5, 2.0) |
| 12 hours | 1.0 (−2.3, 3.0) | 1.1 (−1.0, 5.0) | 1.0 (−0.5, 3.5) | 1.3 (−1.0, 3.0) |
| 24 hours | −1.0 (−4.5, 1.6) | 0.6 (−1.0, 3.5) | 0 (−2.5, 1.0) | −0.3 (−3.3, 2.5) |
| 48 hours | −2.7 (−8.0, 2.0) | 0.7 (−1.5, 3.0) | 0.5 (−2.0, 4.5) | 0 (−4.0, 8.0) |
| 72 hours | −1.5 (−10.0, 7.0) | −0.04 (−2.2, 3.0) | −0.5 (−4.0, 2.5) | 0 (−4.5, 3.0) |
| eGFR ($mL/min/m^2$) | | | | |
| 24 hours | 0.0 (−11.0, 12.1) | 4.0 (−0.4, 15.2) | −0.6 (−6.6, 9.2) | 6.3 (−3.1,16.6) |
| 48 hours | −1.0 (−17.5, 7.0) | 0 (−7.2, 12.0) | −3.4 (−15.4, 13.0) | 0.1 (−12.4, 12.8) |
| 72 hours | −3.5 (−16.6, 16.0) | 0.1 (−10.0, 10.4) | −3.4 (−12.4, 16.7) | 1.6 (−5.9, 11.7) |

cTnT and eGFR are shown as changes from baseline.

Data are shown as median (IQR);

Legend: TnT troponin T; eGFR estimated glomerular filtration rate.

TABLE 7

Troponin percent change from baseline analysis in safety population

| Patients with normal cTnT at baseline Percent change in cTnT >50%, n (%) | Placebo cohort 1 (n = 4) | Istaroxime 0.5 μg/Kg/min (n = 7) | Placebo cohort 2 (n = 5) | Istaroxime 1.0 μg/Kg/min (n = 9) |
|---|---|---|---|---|
| 6 Hours | 2 (50.0%) | 1 (14.3%) | 1 (20.0%) | 0 |
| 12 Hours | 2 (50.0%) | 1 (14.3%) | 0 | 1 (11.1%) |
| 24 Hours | 2 (50.0%) | 1 (14.3%) | 0 | 1 (11.1%) |
| 48 Hours | 1 (25.0%) | 0 | 0 | 3 (33.3%) |
| 72 Hours | 2 (50.0%) | 0 | 1 (20.0%) | 1 (11.1%) |
| **Patients with abnormal cTnT at baseline Percent change in cTnT >20%, n (%)** | **Placebo cohort 1 (n = 15)** | **Istaroxime 0.5 μg/Kg/min (n = 34)** | **Placebo cohort 2 (n = 15)** | **Istaroxime 1.0 μg/Kg/min n (n = 31)** |
| 6 Hours | 2 (13.3%) | 2 (5.9%) | 1 (6.7%) | 5 (16.1%) |
| 12 Hours | 1 (6.7%) | 6 (17.7%) | 4 (26.7%) | 7 (22.6%) |
| 24 Hours | 2 (13.3%) | 4 (11.8%) | 2 (13.3%) | 7 (22.6%) |
| 48 Hours | 2 (13.3%) | 4 (11.8%) | 2 (14.3%) | 7 (22.6%) |
| 72 Hours | 2 (13.3%) | 6 (17.7%) | 0 | 7 (22.6%) |

Data shown as count (%).
Normal/abnormal cTnT defined as baseline cTnT < or ≥ of the 99% URL, respectively (as defined for the Roche high-sensitivity test in patients with normal renal function);
Legend: cTnT cardiac troponin T.

TABLE 8

Holter monitoring parameters

| Variable | Placebo cohort 1 (n = 19) | Istaroxime 0.5 μg/Kg/min (n = 41) | Placebo cohort 2 (n = 20) | Istaroxime 1.0 μg/Kg/min (n = 40) |
|---|---|---|---|---|
| Premature ventricular complexes (n°/24hours) | | | | |
| Screening | 63.0 (1, 1199) | 250.0 (4, 962) | 232.5 (10, 1498) | 84.0 (7, 1195) |
| First day (istaroxime infusion) | 195.5 (4, 1646) | 221.0 (11, 1199) | 292.0 (51, 1813) | 441.0 (49, 1746) |
| Second day | n = 13 380.0 (46, 1020) | n = 25 457.0 (20, 2335) | n = 19 396.0 (52, 1978) | n = 35 197.0 (20, 1191) |
| Ventricular tachycardia, number of patients, n (%) | | | | |
| Screening | 9 (47.4) | 18 (43.9) | 8 (40.0) | 20 (50.0) |
| First day (istaroxime infusion) | 9 (47.4) | 19 (46.3) | 12 (60.0) | 24 (60.0) |
| Second day | 8 (42.1) | 13 (31.7) | 12 (60.0) | 20 (50.0) |
| Ventricular tachycardia, number of episodes | | | | |
| Screening | 3.5 (2.0, 11.0) | 2.0 (1.0, 4.0) | 3.0 (3.0, 5.0) | 2.0 (1.0, 8.0) |
| First day (istaroxime infusion) | 3.5 (2.0, 8.0) | 2.5 (1.0, 4.5) | 1.0 (1.0, 4.0) | 4.0 (1.0, 13.0) |
| Second day | n=8 2.5 (2.0, 8.0) | n=14 1.5 (1.0, 4.0) | n=13 2.0 (1.0, 5.0) | n=20 3.0 (1.0, 4.5) |
| New onset atrial fibrillation, n (%) | | | | |
| Screening | — | — | — | — |
| First day (istaroxime infusion) | — | 1 (2.4) | — | 3 (7.5) |

TABLE 8-continued

| Holter monitoring parameters | | | | |
|---|---|---|---|---|
| Variable | Placebo cohort 1 (n = 19) | Istaroxime 0.5 μg/Kg/min (n = 41) | Placebo cohort 2 (n = 20) | Istaroxime 1.0 μg/Kg/min (n = 40) |
| Second day | — | — | — | 3 (7.5) |
| Presence of clinically significant episodes of supraventricular or ventricular arrhythmias, n (%) | | | | |
| Screening | 2 (10.5) | 1 (2.4) | 4 (20.0) | 4 (10.0) |
| First day (istaroxime infusion) | 2 (10.5) | 1 (2.4) | 4 (20.0) | 4 (10.0) |
| Second day | 2 (10.5) | 1 (2.4) | 4 (20.0) | 3 (12.5) |

(Data are shown as median (IQR) for number of premature ventricular complexes and number of ventricular tachycardia episodes, or as n (%) otherwise)

TABLE 9

| Adverse Events | | | |
|---|---|---|---|
| Event | Placebo (n = 39) | Istaroxime 0.5 μg/Kg/min (n = 41) | Istaroxime 1.0 μg/Kg/min (n = 40) |
| All adverse events | 23 (59.0 | 31 (75.6) | 33 (82.5) |
| Adverse events leading to discontinuation | 1 (2.6) | — | 4 (10.0) |
| Serious adverse events | 2 (5.1) | 2 (4.9) | 6 (15.0) |
| Cardiac death | — | — | 1 (2.5) |
| Cardiogenic shock | — | — | 1 (2.5)[d] |
| Cardiac failure | 1 (2.6) | 2 (4.9) | 3 (7.5) |
| Renal embolism | — | — | 1 (2.5) |
| Transient ischemic attack | 1 (2.6) | — | — |
| Hyperventilation | 1 (2.6) | — | — |
| Hypotension | 1 (2.6) | — | — |
| Adverse drug reactions[a] | 10 (25.6) | 23 (56.1) | 25 (62.5) |
| Cardiovascular[b] | 9 (23.1) | 4 (9.8) | 7 (17.5) |
| Gastrointestinal[c] | 2 (5.1) | 4 (9.8) | 14 (35.0) |
| Infusion site pain/inflammation | — | 20 (48.8) | 13 (32.5) |

Data are shown as number of patients (%). Patients can have more than one event during the 30-day follow-up period.
[a]Adverse events related to study drug.
[b]Most common: arrhythmia, atrial fibrillation, cardiac failure, ventricular tachycardia.
[c]Most common abdominal pain, nausea, vomiting, diarrhea.
[d]Same patient who then died.

Discussion

Our results show that a 24 h infusion of istaroxime at 0.5 or 1.0 μg/kg/min in patients with AHF and reduced LVEF improves left ventricular diastolic and systolic function without an increase in major cardiac AEs. The primary endpoint of our study (E/e' ratio change from baseline to 24 h) was significantly reduced by both doses of istaroxime compared to placebo. Other parameters related to left ventricular diastolic function (i.e. E/A wave ratio and left atrial dimensions) were also reduced with istaroxime. Among the parameters related with left ventricular systolic function, stroke volume index increased with istaroxime compared to placebo, though the increase in LVEF did not reach statistical significance. These effects were accompanied by a decrease in HR and an increase in SBP, which reached statistical significance with the 1.0 μg/kg/min dose. These latter changes occurred early after the start of the infusion, with significant differences already evident at 3 h. This is consistent with the pharmacokinetic profile of istaroxime, which has a very rapid onset of action and a similar fast washout after infusion termination, making this drug suitable for the use in high-risk patients and potentially in critically ill patients. As observed in this study, possible rebound effects should be taken into account, since a mild increase in HR was present at 48 h in the high-dose group. This would probably require a down-titration phase before withdrawal in patients receiving high dose in future studies.

The overall diuresis during the infusion period was higher in patients treated with istaroxime, consistently with the change in E/e ratio. A favorable effect on renal function was observed with istaroxime, with an increase in eGFR with the high dose compared to placebo at 24 h. Absolute troponin levels did not differ between the istaroxime and placebo groups, and no major untoward effects, including no increase in arrhythmias, were observed. Despite being frequent, especially with high-dose istaroxime, gastrointestinal symptoms required stopping of infusion only in one patient due to nausea and in a second patient due to vomiting which occurred concomitantly to a SAE (renal artery embolism attributed to a pre-existing ventricular thrombus). The proportion of patients experiencing injection site reactions was high, requiring the change of the peripheral line or a shift to a peripheral long line or a central line. However, only one patient (treated with istaroxime 1.0 μg/kg/min) discontinued the study drug due to this AE. These findings support the hypothesis that despite frequent side effects, the overall tolerability of istaroxime was acceptable. Our results confirm and extend to a 24 h infusion the findings of HORIZON-HF, where a 6 h istaroxime infusion was tested. Different from HORIZON-HF where patients underwent right heart catheterization, we used a non-invasive assessment based on Doppler echocardiography for practical purposes. The assessment of the effects of a 24 h infusion was mandatory for the clinical development of this drug, as a short-term 6 h administration is unlikely to be sufficient for symptom relief and haemodynamic stabilization in clinical practice. Our results demonstrated persistent and adjunctive favorable hemodynamic effects of istaroxime at 24 h and also provide more data on drug safety. Treatment of patients hospitalized for AHF with low or borderline SBP remains a major unmet need. Low SBP identifies patients who are at an extremely high risk of death. No safe and effective therapy has emerged for these patients, and inotropes have been associated with major cardiovascular AEs and possibly increased mortality. The mechanism of action and the hemodynamic effects of istaroxime provide the potential for improving clinical outcomes in these patients. Istaroxime has favorable effects on left ventricular diastolic and systolic function without increasing free cytoplasmic calcium levels, the possible mechanism of the arrhythmogenic and toxic effects of digoxin, catecholamines, and phosphodiesterase inhibitors on cardiac myocytes. A sustained increase in SBP was observed with both doses of istaroxime, reaching significance with the higher dose. Together with improvement in renal function, these effects suggest better organ perfusion, making the drug potentially attractive for the treatment of patients with hypotension and low cardiac output. These hemodynamic effects appear to be obtained with no increase in HR, whereas tachycardia caused by traditional inotropic agents is a major determinant of increased myocardial oxygen consumption and ischaemia. In addition, no clinical events related to myocardial ischemia with istaroxime, compared to placebo, were observed in our study.

Limitations

The major limitation of this study relates to enrollment discrepancies between the study populations and sites of the two cohorts, with cohort 2 enrolling exclusively Asian patients. We observed that patients enrolled in this trial were younger and had better renal function compared with other studies. Of note, an interim analysis showed similar echocardiographic characteristics between different ethnic groups within cohort 1. Although variation in AHF patients' management cannot be excluded, these differences may have had a limited impact on the primary endpoint and our results are consistent with previous data from the HORIZON-HF trial. In addition, the efficacy and safety analyses were performed by blinded central laboratories with a robust and uniform methodology and our results showed similar effects of istaroxime in both cohorts. Istaroxime promoting SERCA2a activity has a direct effect on a pathophysiological pathway that may represent the common cardiac mechanism at the basis of heart failure progression, thus overcoming the heterogeneity in AHF populations, which is probably one of the most important causes of the failure of several investigational drugs in this area. Our study was powered to detect a significant change in the E/e ratio at 24 h with istaroxime vs. placebo. Estimation of the size of the study group was based on previous data, and the study achieved its primary endpoint. However, other parameters such as LVEF and left ventricular volumes may have a larger variability with echocardiography compared to the invasive assessment, and/or are less affected by a 24 h infusion of the study drug. A larger study group would be required to ascertain istaroxime effects on these parameters. In addition, enrolling patients closer to admission will likely be required to show istaroxime effects on the patient symptoms and clinical course.

Conclusions

This randomized, double-blind, placebo-controlled, phase II trial shows that a 24 h infusion of istaroxime in patients hospitalized for AHF improves parameters of left ventricular systolic and diastolic function, with a decrease in HR and maintenance or increase of SBP at low and high dose, respectively. This study represents a proof-of-concept that SERCA2a stimulation is a novel and valid target for the treatment of patients with AHF. Despite most clinical trials in this clinical context failed to confirm preliminary results in larger trials, this drug may have potential benefits in a more selected population of patients with low blood pressure and low cardiac output, which represents a high-risk group with poor outcomes and no evidence of safe and effective treatments. Further research evaluating istaroxime effects on clinical symptoms, clinical course, and outcomes is warranted in such targeted population.

REFERENCES

1. Ponikowski P, Voors A A, Anker S D, Bueno H, Cleland J G, Coats A J, Falk V, González-Juanatey J R, Harjola V P, Jankowska E A, Jessup M, Linde C, Nihoyannopoulos P, Parissis J T, Pieske B, Riley J P, Rosano G M, Ruilope L M, Ruschitzka F, Rutten F H, van der Meer P. 2016 ESC guidelines for the diagnosis and treatment of acute and chronic heart failure: The Task Force for the diagnosis and treatment of acute and chronic heart failure of the European Society of Cardiology (ESC). Developed with the special contribution of the Heart Failure Association (HFA) of the ESC. Eur J Heart Fail 2016; 18:891-975.
2. Yancy C W, Jessup M, Bozkurt B, Butler J, Casey D E Jr, Drazner M H, Fonarow G C, Geraci S A, Horwich T, Januzzi J L, Johnson M R, Kasper E K, Levy W C, Masoudi F A, McBride P E, McMurray J J, Mitchell J E, Peterson P N, Riegel B, Sam F, Stevenson L W, Tang W H, Tsai E J, Wilkoff B L. 2013 ACCF/AHA guideline for the management of heart failure: executive summary: a report of the American College of Cardiology Foundation/American Heart Association Task Force on Practice Guidelines. Circulation 2013:128:1810-1852.
3. Mebazaa A, Yilmaz M B, Levy P, Ponikowski P, Peacock W F, Laribi S, Ristic A D, Lambrinou E, Masip J, Riley J P, McDonagh T, Mueller C, deFilippi C, Harjola V P, Thiele H, Piepoli M F, Metra M, Maggioni A, McMurray J, Dickstein K, Damman K, Seferovic P M, Ruschitzka F, Leite-Moreira A F, Bellou A, Anker S D, Filippatos G. Recommendations on pre-hospital & early hospital management of acute heart failure: a consensus paper from the Heart Failure Association of the European Society of Cardiology, the European Society of Emergency Medicine and the Society of Academic Emergency Medicine. Eur J Heart Fail 2015; 17: 544-558.
4. Gheorghiade M, Abraham W T, Albert N M, Greenberg B H, O'Connor C M, She L, Stough W G, Yancy C W, Young J B, Fonarow G C: OPTIMIZE-HF Investigators and Coordinators. Systolic blood pressure at admission, clinical characteristics, and outcomes in patients hospitalized with acute heart failure. JAMA 2006:296:2217-2226.
5. Metra M, Bettari L, Carubelli V, Dei Cas L. Old and new intravenous inotropic agents in the treatment of advanced heart failure. Prog Cardiovasc Dis 2011:54:97-106.
6. Hasenfuss G, Teerlink J R. Cardiac inotropes: current agents and future directions. Eur Heart J 2011:32:1838-1845.
7. Psotka M A, Gottlieb S S, Francis G S, Allen L A, Teerlink J R, Adams K F Jr, Rosano G M, Lancellotti P. Cardiac calcitropes, myotropes, and mitotropes: JACC review topic of the week. J Am Coll Cardiol 2019:73:2345-2353.
8. Mebazaa A, Motiejunaite J, Gayat E, Crespo-Leiro M G, Lund L H, Maggioni A P, Chioncel O, Akiyama E, Harjola V P, Seferovic P, Laroche C, Julve M S, Roig E, Ruschitzka F, Filippatos G: ESC Heart Failure Long-Term Registry Investigators. Long-term safety of intravenous cardiovascular agents in acute heart failure: results from the European Society of Cardiology Heart Failure Long-Term Registry. Eur J Heart Fail 2018:20:332-341.
9. Maack C, Eschenhagen T, Hamdani N, Heinzel F R, Lyon A R, Manstein D J, Metzger J, Papp Z, Tocchetti C G, Yilmaz M B, Anker S D, Balligand J L, Bauersachs J, Brutsaert D, Carrier L, Chlopicki S, Cleland J G, de Boer R A, Dietl A, Fischmeister R, Harjola V P, Heymans S, Hilfiker-Kleiner D, Holzmeister J, de Keulenaer G, Limongelli G, Linke W A, Lund L H, Masip J, Metra M, Mueller C, Pieske B, Ponikowski P, Risti'c A, Ruschitzka F, Seferovi'c PM, Skouri H, Zimmermann W H, Mebazaa A. Treatments targeting inotropy. Eur Heart J 2019; 40:3626-3644.

10. Ferrandi M, Barassi P, Tadini-Buoninsegni F, Bartolommei G, Molinari I, Tripodi M G, Reina C, Moncelli M R, Bianchi G, Ferrari P. Istaroxime stimulates SERCA2a and accelerates calcium cycling in heart failure by relieving phospholamban inhibition. Br J Pharmacol 2013:169: 1849-1861.

11. Micheletti R, Palazzo F, Barassi P, Giacalone G, Ferrandi M, Schiavone A, Moro B, Parodi O, Ferrari P, Bianchi G. Istaroxime, a stimulator of sarcoplasmic reticulum calcium adenosine triphosphatase isoform 2a activity, as a novel therapeutic approach to heart failure. Am J Cardiol 2007:99:24A-32A.

12. Gheorghiade M, Ambrosy A P, Ferrandi M, Ferrari P. Combining SERCA2a activation and Na-K ATPase inhibition: a promising new approach to managing acute heart failure syndromes with low cardiac output. Discov Med 2011:12:141-151.

13. Rocchetti M, Besana A, Mostacciuolo G, Micheletti R, Ferrari P, Sarkozi S, Szegedi C, Jona I, Zaza A. Modulation of sarcoplasmic reticulum function by Na+/K+ pump inhibitors with different toxicity: digoxin and PST2744 [(E,Z)-3-((2-aminoethoxy)imino)androstane-6, 17-dione hydrochloride]. J Pharmacol Exp Ther 2005: 313:207-215.

14. Teerlink J R, Metra M, Zacà V, Sabbah H N, Cotter G, Gheorghiade M, dei Cas L. Agents with inotropic properties for the management of acute heartfailure syndromes. Traditional agents and beyond. Heart Fail Rev 2009; 14: 243-253.

15. Gheorghiade M, Blair J E, Filippatos G S, Macarie C, Ruzyllo W, Korewicki J, Bubenek-Turconi S I, Ceracchi M, Bianchetti M, Carminati P, Kremastinos D, Valentini G, Sabbah H N: HORIZON-HF Investigators. Hemodynamic, echocardiographic, and neurohormonal effects of istaroxime, a novel intravenous inotropic and lusitropic agent: a randomized controlled trial in patients hospitalized with heart failure. J Am Coll Cardiol 2008:51:2276-2285.

16. Shah S J, Blair J E, Filippatos G S, Macarie C, Ruzyllo W, Korewicki J, Bubenek-Turconi S I, Ceracchi M, Bianchetti M, Carminati P, Kremastinos D, Grzybowski J, Valentini G, Sabbah H N, Gheorghiade M: HORIZON-HF Investigators. Effects of istaroxime on diastolic stiffness in acute heart failure syndromes: results from the Hemodynamic, Echocardiographic, and Neurohormonal Effects of Istaroxime, a novel intravenous inotropic and lusitropic agent: a randomized controlled trial in patients hospitalized with heart failure (HORIZON-HF) trial. Am Heart J 2009:157:1035-1041.

17. Gheorghiade M, Sabbah H N. Istaroxime: an investigational luso-inotropic agent for acute heart failure syndromes. Am J Cardiol 2007:99:1A-3A.

18. Khan H, Metra M, Blair J E, Vogel M, Harinstein M E, Filippatos G S, Sabbah H N, Porchet H, Valentini G, Gheorghiade M. Istaroxime, a first in class new chemical entity exhibiting SERCA-2 activation and Na-K-ATPase inhibition: a new promising treatment for acute heart failure syndromes? Heart Fail Rev 2009:14:277-287.

19. Butler J, Gheorghiade M, Kelkar A, Fonarow G C, Anker S, Greene S J, Papadimitriou L, Collins S, Ruschitzka F, Yancy C W, Teerlink J R, Adams K, Cotter G, Ponikowski P, Felker G M, Metra M, Filippatos G. In-hospital worsening heart failure. Eur J Heart Fail 2015:17:1104-1113.

20. Nagueh S F, Appleton C P, Gillebert T C, Marino P N, Oh J K, Smiseth O A, Waggoner A D, Flachskampf F A, Pellikka P A, Evangelisa A. Recommendations for the evaluation of left ventricular diastolic function by echocardiography. Eur J Echocardiogr 2009:10:165-193.

21. Gheorghiade M, Vaduganathan M, Ambrosy A, Böhm M, Campia U, Cleland J G, Fedele F, Fonarow G C, Maggioni A P, Mebazaa A, Mehra M, Metra M, Nodari S, Pang P S, Ponikowski P, Sabbah H N, Komajda M, Butler J. Current management and future directions for the treatment of patients hospitalized for heart failure with low blood pressure. Heart Fail Rev 2013:18:107-122.

22. Chioncel O, Mebazaa A, Harjola V P, Coats A J, Piepoli M F, Crespo-Leiro M G, Laroche C, Seferovic P M, Anker S D, Ferrari R, Ruschitzka F, Lopez-Fernandez S, Miani D, Filippatos G, Maggioni A P; ESC Heart Failure Long-Term Registry Investigators. Clinical phenotypes and outcome of patients hospitalized for acute heart failure: the ESC Heart Failure Long-Term Registry. Eur J Heart Fail 2017; 19:1242-1254.

23. Thackray S, Easthaugh J, Freemantle N, Cleland J G. The effectiveness and relative effectiveness of intravenous inotropic drugs acting through the adrenergic pathway in patients with heart failure—a meta-regression analysis. Eur J Heart Fail 2002; 4:515-529.

What is claimed:

1. A method of treating acute heart failure in a subject in need thereof, comprising administering a therapeutically effective amount of istaroxime by intravenous infusion over a period of at least 24 hours, wherein the therapeutically effective amount of istaroxime is between about 0.1 μg/kg/min and about 3.0 μg/kg/min, wherein administering a therapeutically effective amount of istaroxime does not result in a significant change in at least one of heart rate, myocardial energy consumption, brain natriuretic peptide (BNP) levels, N-terminal pro BNP (NT-proBNP) levels, and cardiac troponin levels, thereby treating the subject's acute heart failure.

2. The method of claim 1, wherein the subject has at least one of low cardiac output, hypotension, low systolic blood pressure, reduced left ventricular ejection fraction, intermediate to high E/e' ratio, a resting heart rate between about 50 and about 120 beats per minute, a potassium level between about 3.8 and about 5.3 mmol/L, and a serum creatinine level greater than 3.0 mg/dL or an estimated glomerular filtration rate (eGFR) greater than 30 mL/min/$m^2$ prior to administrating a therapeutically effective amount of istaroxime.

3. The method of claim 1, wherein the subject is hospitalized for acute heart failure, prior to administering a therapeutically effective amount of istaroxime.

4. The method of claim 1, wherein the subject:

(i) is not receiving concomitant treatment with intravenous vasodilators, inotropes, vasopressors, oral digoxin or any combination thereof prior to administering a therapeutically effective amount of istaroxime;

(ii) is resistant to diuretics, vasodilators, or a combination thereof; or (iii) both (i) and (ii).

5. The method of claim 1, wherein administering a therapeutically effective amount of istaroxime results in a decreased heart rate, an increase in systolic blood pressure, or both.

6. The method of claim 1, wherein administering a therapeutically effective amount of istaroxime results in a decreased heart rate by about 3 to about 9 beats per minute.

7. The method of claim 1, wherein administering a therapeutically effective amount of istaroxime results in an increase in systolic blood pressure by about 15 mmHg.

8. The method of claim 1, wherein administering a therapeutically effective amount of istaroxime results in an increase in systolic blood pressure by about 3 to about 8 mmHg.

9. The method of claim 1, wherein administering a therapeutically effective amount of istaroxime results in an improvement in cardiac function without tachycardia or hypotension.

10. The method of claim 1, wherein administering a therapeutically effective amount of istaroxime results in at least one of increased cardiac contractility, increased myocardial relaxation, increased ventricle relaxation, increased rate of myocardial relaxation, increased inotropy, increased left ventricular systolic function, increased stroke volume index, increased afterload associated with decreased E'no ", increased renal function, increased organ reperfusion, increased left ventricular ejection fraction, and increased diuresis.

11. The method of claim 1, wherein administering a therapeutically effective amount of istaroxime results in an increase in renal function.

12. The method of claim 1, wherein administering a therapeutically effective amount of istaroxime does not result in at least one of major cardiac adverse events, myocardial ischemia, hypotension, tachycardia, arrhythmias, end organ damage, and increased mortality.

13. The method of claim 1, wherein administering a therapeutically effective amount of istaroxime results in an improvement in cardiac function without end organ damage.

14. The method of claim 1, wherein treatment is observable for up to 48 hours.

15. The method of claim 3, wherein administering a therapeutically effective amount of istaroxime results in a decreased risk of readmissions or emergency visits for cardiovascular reasons for at least 30 days after administration, a reduced risk of episodes of in-hospital worsening heart failure for at least 4 days after administration, or both.

16. The method of claim 1, further comprising a downward titration of istaroxime following intravenous infusion over a period of at least 24 hours.

17. The method of claim 1, further comprising administering a diuretic.

18. The method of claim 1 further comprising administering at least 20 mg intravenous furosemide.

19. The method of claim 1, further comprising administering an antiemetic if the subject experiences gastrointestinal upset.

* * * * *